United States Patent
Qi

(10) Patent No.: US 10,032,297 B2
(45) Date of Patent: Jul. 24, 2018

(54) SIMULATION SYSTEM, SIMULATION DEVICE, AND PRODUCT EXPLANATION ASSISTANCE METHOD

(71) Applicant: HOYA CORPORATION, Tokyo (JP)

(72) Inventor: Hua Qi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/766,277

(22) PCT Filed: Nov. 13, 2013

(86) PCT No.: PCT/JP2013/080632
§ 371 (c)(1),
(2) Date: Aug. 6, 2015

(87) PCT Pub. No.: WO2014/122834
PCT Pub. Date: Aug. 14, 2014

(65) Prior Publication Data
US 2015/0371415 A1 Dec. 24, 2015

(30) Foreign Application Priority Data

Feb. 6, 2013 (JP) ................................ 2013-021112

(51) Int. Cl.
*G09G 5/14* (2006.01)
*G06T 11/20* (2006.01)
(Continued)

(52) U.S. Cl.
CPC ............ *G06T 11/20* (2013.01); *A61B 3/0025* (2013.01); *G02C 7/028* (2013.01);
(Continued)

(58) Field of Classification Search
CPC ................................................... G06T 11/60
(Continued)

(56) References Cited

U.S. PATENT DOCUMENTS

2003/0076479 A1  4/2003  Qi
2009/0248377 A1*  10/2009  Shinohara ............ A61B 3/0025
703/6
(Continued)

FOREIGN PATENT DOCUMENTS

JP  2003-177076 A  6/2003
JP  2008-250441 A  10/2008
(Continued)

OTHER PUBLICATIONS

Sep. 20, 2016 Extended Search Report issued in European Patent Application No. 13874426.3.
(Continued)

*Primary Examiner* — Javid A Amini
(74) *Attorney, Agent, or Firm* — Oliff PLC

(57) ABSTRACT

In a simulation system in which a terminal device employed in a spectacle shop and a display device for visually recognizing by a prospective spectacle lens wearer, are connected to a server device so as to capable of communication: the server device includes an image generation unit that achieves a state in which a simulation image reflecting lens visual performance of a spectacle lens can be output for each of plural partial visual field areas, and an information storage unit that stores explanatory information regarding characteristics of the lens visual performance for each of the plural partial visual field areas; the display device includes a display screen unit that selectively displays the simulation images in the partial visual field areas; and the terminal device includes an information output unit that outputs the explanatory information corresponding to the partial visual field area being displayed on the display screen unit.

12 Claims, 14 Drawing Sheets

(51) Int. Cl.
  *A61B 3/00* (2006.01)
  *G02C 7/02* (2006.01)
  *G06Q 30/06* (2012.01)
  *G06T 3/00* (2006.01)
  *G06T 11/60* (2006.01)
  *G06T 19/00* (2011.01)

(52) U.S. Cl.
  CPC ....... *G06Q 30/0621* (2013.01); *G06T 3/0093* (2013.01); *G06T 11/60* (2013.01); *G06T 19/006* (2013.01)

(58) Field of Classification Search
  USPC ........................................................ 345/633
  See application file for complete search history.

(56) References Cited

U.S. PATENT DOCUMENTS

| | | | |
|---|---|---|---|
| 2010/0091027 A1* | 4/2010 | Oyama | G02B 27/0068 345/581 |
| 2010/0114540 A1* | 5/2010 | Shinohara | G01M 11/0257 703/1 |
| 2011/0230751 A1 | 9/2011 | Kersting | |
| 2013/0278631 A1* | 10/2013 | Border | G02B 27/017 345/633 |
| 2013/0335543 A1* | 12/2013 | Hilkes | H04N 7/185 348/62 |

FOREIGN PATENT DOCUMENTS

| | | |
|---|---|---|
| JP | 2012-506272 A | 3/2012 |
| JP | 2012-066002 A | 4/2012 |
| KR | 1020090033122 A | 4/2009 |
| WO | 2009/133887 A1 | 11/2009 |
| WO | 2010/044383 A1 | 4/2010 |

OTHER PUBLICATIONS

Jan. 28, 2014 International Search Report issued in International Patent Application No. PCT/JP2013/080632.

Jan. 28, 2014 Written Opinion issued in International Patent Application No. PCT/JP2013/080632.

* cited by examiner

SIMULATION SYSTEM, SIMULATION DEVICE, AND PRODUCT EXPLANATION ASSISTANCE METHOD

TECHNICAL FIELD

The present invention relates to a simulation system, a simulation device, and a product explanation assistance method for giving a prospective spectacle lens wearer a simulated experience of what it is like to look through a spectacle lens scheduled to be worn.

BACKGROUND ART

Hitherto simulation devices have been employed in a spectacle shop to give a prospective spectacle lens wearer a simulated experience of a state of wearing spectacle a lens (see, for example, Patent Document 1). Using the simulation device enables a prospective spectacle lens wearer to physically experience what it is like to look through the spectacle lens (distortion, blur, etc. of images) by checking a simulation image by sight before ordering the lens. Image forming by simulation is also employed at the spectacle shop side to enable a prospective spectacle lens wearer to physically experience what it is like to when looking through a worn lens of a sort of lens lacking a sample lens, without requiring preparation of sample lens to the lens prescription or the like desired by the prospective spectacle lens wearer.

In particular, progressive addition lenses that include a free curved surface of an individualized design are recently starting to become widespread as spectacle lenses. An appropriate lens design standard for such progressive addition lenses is selected according to the lifestyle of the prospective spectacle lens wearer, conditions of spectacle use, etc., and optical design is performed according to the selected lens design standard (see, for example, Patent Document 2). It has accordingly become difficult to prepare sample lenses in advance since optimally customized spectacle lenses can be obtained for each individual prospective spectacle lens wearer, and it has become extremely useful to use simulation devices that allow a simulated experience to be given of a lens wearing state by using a simulation device.

RELATED TECHNICAL DOCUMENTS

Patent Documents

Patent Document 1: International Publication (WO) 2010/044383
Patent Document 2: WO 2009/133887

SUMMARY OF INVENTION

Technical Problem

However, in progressive addition lens having a free curved surface of individualized design, characteristics in lens design generally differ according to the lens design standard applied. This means that characteristics of lens visual performance differ according to the lens design standard applied. Namely, due to characteristics of lens visual performance differing according to the lens design standard applied, what it is like to look through the spectacle lens also differs. What it is like to look through the spectacle lens is also different between respective areas, called a far vision area, a near vision area, an intermediate vision area, and the like. Thus when a simulation device is utilized, not only is it important for a prospective spectacle lens wearer who experiences a simulation of a lens wearing state to be informed of, and given sufficient understanding of, the differences in characteristics in the lens visual performance of the spectacle lens, but determining suitability based on the result of simulated experience is also extremely important to giving the prospective spectacle lens wearer a feeling of satisfaction.

Thus even though conventional simulation devices are able to give a prospective spectacle lens wearer a simulated experience of looking through a spectacle lens, it cannot be said that the prospective spectacle lens wearer is always given sufficiently able to ascertain the differences in characteristics of lens visual performance for each of the spectacle lenses. For example, in the case of a progressive addition lens having a free curved surface of individualized design, several hundreds of sorts of design type are achieved by combination of the lens visual performance characteristics of each of the lenses. Thus there is a concern that it might not be possible to accurately notify and give understanding to the prospective spectacle lens wearer regarding which characteristics of lens visual performance the spectacle lens selected by the prospective spectacle lens wearer possesses, unless there is a member of staff who sufficiently understands the differences in characteristics between the respective several hundreds of sorts of design type achieved. Namely, in order to explain the characteristics of the lens visual performance of the spectacle lens that has been selected by the prospective spectacle lens wearer, a high level of skill in understanding lens design and in explaining is required in the member of staff of the spectacle shop. Thus, depending on the skills of the member of staff, it might not be possible to give a prospective spectacle lens wearer sufficient understanding of the characteristics of lens visual performance of the spectacle lens, and, as a result, the prospective spectacle lens wearer might feel dissatisfied.

Moreover, there is a conventional simulation device in which configuration is made such that the simulation image is displayed on a display screen of a head mounted display (HMD) when having a prospective spectacle lens wearer check a simulation image by sight (see, for example, Patent Document 1). However, when giving a simulated experience of a lens wearing state using a HMD, there are few HMDs capable of reproducing the full visual field of the spectacle lens with clarity, and those capable of reproducing the full visual field with clarity have a high cost for introduction into spectacle shops, and, because of such aspects as their size and weight, are also a burden on the prospective spectacle lens wearers. Moreover, although there are compact, lightweight, low cost HMDs, such HMDs have a limited visual field, and are not sufficient for performing simulation at high resolution. Thus it is possible that conventional simulation devices do not only feel unsatisfactory to the prospective spectacle lens wearers, but also to the spectacle shop side.

Thus an object of the present invention is to provide a simulation system, a simulation device, and a product explanation assistance method that are capable of eliminating the dissatisfaction described above, for the prospective spectacle lens wearer, spectacle shop side, etc., when a prospective spectacle lens wearer is given a simulated experience of a lens wearing state.

Solution to Problem

The present invention is proposed in order to achieve the above object.

In order to achieve the above object, the inventors of the present application first investigated characteristics of lens visual performance of spectacle lenses. Characteristics of lens visual performance, for example for progressive addition lenses having a free curved surface of individualized design, differ by design type of the spectacle lens, and moreover differ between respective areas, called a far vision area, a near vision area, an intermediate vision area and the like. It is accordingly considered extremely difficult for anyone to ascertain all the differences in the several hundred sorts of characteristics achieved through combination.

In consideration thereof, the inventors of the present application have performed further diligent investigations. The inventors of the present application have discovered that characteristics of lens visual performance can be accurately and easily ascertained for lens visual performance that varies by lens design type and between respective areas by preparing explanatory information regarding the characteristics by design type and by area, and outputting explanatory information corresponding to display content that matches display of a simulation image to the prospective spectacle lens wearer. Moreover, in displaying the simulation image, it has been discovered that rather than displaying a full visual field area of the spectacle lens all at once, by segmenting the full visual field area into plural partial visual field areas, and selectively outputting separately for each of the plural partial visual field areas, not only is output of the corresponding explanatory information achieved simply, but it is also possible to clearly check the full visual field area of the spectacle lens by sight, irrespective of size, resolution, and the like of the field of view on the image display side.

The present invention is based on the above new discovery of the inventors of the present application.

A first aspect of the present invention is A simulation system in which a terminal device employed in a spectacle shop, a display device for visually recognizing by a prospective spectacle lens wearer visiting the spectacle shop, and a server device including functionality of a computer, are connected together so as to capable of communication, wherein:

the server device includes
an image generation unit that, based on lens design data of a spectacle lens the prospective spectacle lens wearer is scheduled to wear, performs image processing on an original image for plural partial visual field areas configuring a full visual field area of the spectacle lens to reflect lens visual performance of the spectacle lens, and generates a simulation image separately for each of the plural partial visual field areas, and
an information storage unit that stores explanatory information regarding characteristics of the lens visual performance for each of the plurality of partial visual field areas associated with the partial visual field areas, classified by sort of lens design standard applied to the lens design data;
the display device includes a display screen unit that selectively displays the simulation images separately for each of the plurality of partial visual field areas to get the prospective spectacle lens wearer to check by sight; and
the terminal device includes an information output unit that outputs the explanatory information acquired from the information storage unit corresponding to the partial visual field area being displayed on the display screen unit of the display device.

A second aspect of the present invention is the invention of the first aspect, wherein the image generation unit of the server device performs superimposition processing of contour lines of a clearness index of the spectacle lens onto the simulation image, and the display screen unit of the display device displays the simulation image with the contour lines superimposed.

A third aspect of the present invention is the invention of the first or the second aspect, wherein
the image generation unit of the server device performs overlay processing of overlaying a frame image of a spectacle frame on the simulation image for holding the spectacle lens; and
the display screen unit of the display device displays the simulation image on which the frame image is overlaid.

A fourth aspect of the present invention is the invention of the first, second, or third aspect, wherein the display device is a head mounted display device worn on the head of the prospective spectacle lens wearer, and the display screen unit performs image display individually for the left eye and right eye of the prospective spectacle lens wearer.

A fifth aspect of the present invention is the invention of any aspect from the first to the fourth aspect, wherein the terminal device is a portable information terminal used by a member of staff of the spectacle shop, and the information output unit displays output of the explanatory information to the member of staff.

A sixth aspect of the present invention is the invention of any aspect from the first to the fifth aspect, wherein the information output unit audio-outputs the explanatory information.

A seventh aspect of the present invention is the invention of any aspect from the first to the sixth aspect, wherein an operation unit for performing a selection operation of a partial visual field area to display on the display device is provided to at least one out of the display device or the terminal device.

An eighth aspect of the present invention is the invention of any one of the first to the seventh aspect, wherein: the terminal device includes an information input unit for inputting parameter information for the spectacle lens scheduled to be worn by the prospective spectacle lens wearer; and the server device includes a data generation unit that, based on the parameter information that has been input by the information input unit, identifies the sort of lens design standard that should be applied to a spectacle lens scheduled to be worn by the prospective spectacle lens wearer, and that generates lens design data of the spectacle lens while applying a lens design standard of the identified sort.

A ninth aspect of the present invention is a simulation device configured with a terminal device employed in a spectacle shop, and a display device for visually recognizing by a prospective spectacle lens wearer visiting the spectacle shop, connected together so as to be capable of communication, the display device includes a display screen unit that selectively displays a simulation image, obtained by performing image processing to reflect lens visual performance of the spectacle lens on an original image for a plurality of partial visual field areas constituting a full visual field area of a spectacle lens, separately for each of the partial visual field areas to get the prospective spectacle lens wearer to check by sight; and
the terminal device includes an information output unit that outputs explanatory information regarding characteristics of the lens visual performance reflected in a partial visual field area being displayed on the display screen unit of the display device.

A tenth aspect of the present invention is the invention of the ninth aspect, wherein: at least one out of the terminal device or the display device is connected to a communication network and includes a communication interface that performs communication with a server device over the communication network; and configuration is made such that at least the simulation image and the explanatory information are acquired from the server device through the communication interface separately for each of the partial visual field areas.

An eleventh aspect of the present invention is the invention of the ninth aspect, wherein at least one out of the terminal device or the display device includes an information storage unit that stores the simulation image and the explanatory information separately for each of the partial visual field areas.

A twelfth aspect of the present invention is a product explanation assistance method for assisting a product explanation during a product explanation performed at the spectacle shop, by using a terminal device employed in a spectacle shop, and a display device for visually recognizing a simulation image by a prospective spectacle lens wearer visiting the spectacle shop, the product explanation assistance method comprising:

an image display step in which a simulation image, obtained by performing image processing to reflect lens visual performance of a spectacle lens on an original image for plural partial visual field areas configuring a full visual field area of the spectacle lens, is selectively displayed on the display device separately for each of the plural partial visual field areas to get to the prospective spectacle lens wearer to check by sight;

an information output step of acquiring from an information storage unit, and outputting to the terminal device, explanatory information regarding characteristics of the lens visual performance reflected in partial visual field areas for display on the display device and that has been stored in advance in an associated state of the partial visual field areas and the explanatory information; and a selection switching step of switching selection of partial visual field area for displaying on the display device and correspondingly switching explanatory information for outputting by the terminal device.

Advantageous Effects of Invention

The present invention enables sufficient understanding of the characteristics of lens visual performance of a spectacle lens to be given to a prospective spectacle lens wearer when giving a prospective spectacle lens wearer a simulated experience of a lens wearing state, and moreover enables clear checking of the full visual field of the spectacle lens by sight.

DESCRIPTION OF EMBODIMENTS

Explanation follows regarding embodiments of the present invention, with reference to the drawings.

Explanation of the present embodiments will be split into sections in the following sequence.

Figure 1:
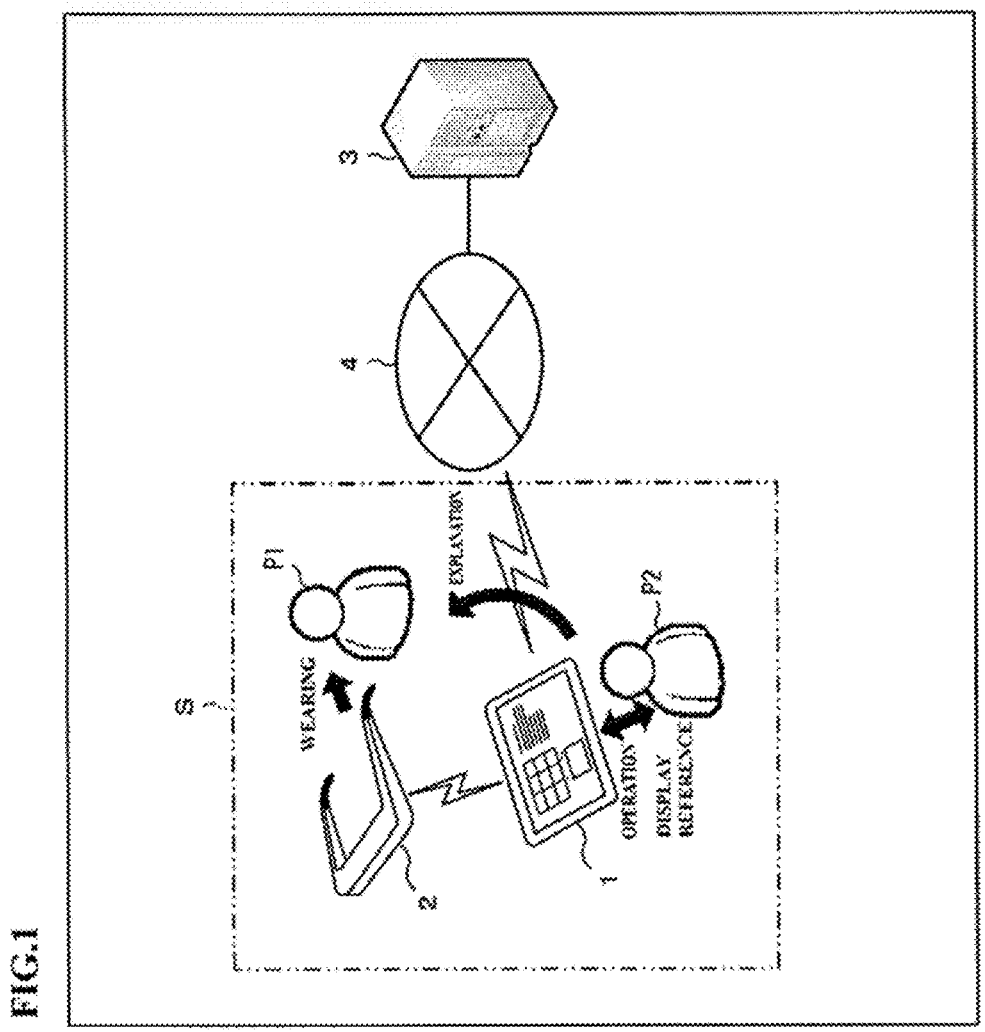
FIG. 1 is a schematic diagram illustrating an example of an outline configuration of an overall simulation system of a first embodiment of the present invention.

A. First Embodiment
  1. Schematic Overall Configuration of Simulation System.
  2. Functional Configuration of Simulation System.
  3. Procedure of Simulation Processing in Spectacle shop.
  4. Advantageous Effects of Present Embodiment
B. Second Embodiment
C. Modified Examples etc.
  A. First Embodiment
  Explanation first follows regarding the first embodiment of the present invention.
  1. Schematic Overall Configuration of Simulation System
  First explanation follows regarding a schematic overall configuration of a simulation system of the present embodiment.
  FIG. 1 is a schematic diagram illustrating an example of a schematic overall configuration of a simulation system of the present embodiment.

The simulation system in the present embodiment is employed on a prospective spectacle lens wearer P1 who has visited a spectacle shop S, and is employed to give the prospective spectacle lens wearer P1 a simulated experience of what it is like to look through the spectacle lens that the prospective spectacle lens wearer P1 is scheduled to wear. The simulation system accordingly includes a terminal device 1 employed in the spectacle shop S, a display device 2 equipped with a display screen unit for the prospective spectacle lens wearer P1 who has visited the spectacle shop S to check by sight, and a server device 3 including the functions of a computer, in a configuration connected together to enable communication through a communication network 4 such as the internet. An example is illustrated here of a case provided with one each of the terminal device 1, the display device 2, and the server device 3, however plural of the terminal devices 1 and the display devices 2 (namely plural of the spectacle shops S) may be connected to a single server device 3.

A portable data terminal (referred to below as a "tablet terminal") for use by a member of staff P2 at the spectacle shop S is, for example, employed as the terminal device 1. Explanation follows regarding an example of a case in the present embodiment in which the terminal device 1 is a tablet terminal, explained below.

A head mounted display (referred to below as "HMD") that is mounted to the head of the prospective spectacle lens wearer P1 is, for example, employed as the display device 2. Explanation follows regarding an example of a case in the present embodiment in which the display device 2 is a HMD.

The tablet terminal 1 and the HMD 2 are employed in the spectacle shop S, and a simulation device, described later, is configured thereby.

2. Functional Configuration of Simulation System

Explanation next follows regarding a functional configuration of the simulation system of the present embodiment.

Figure 2:
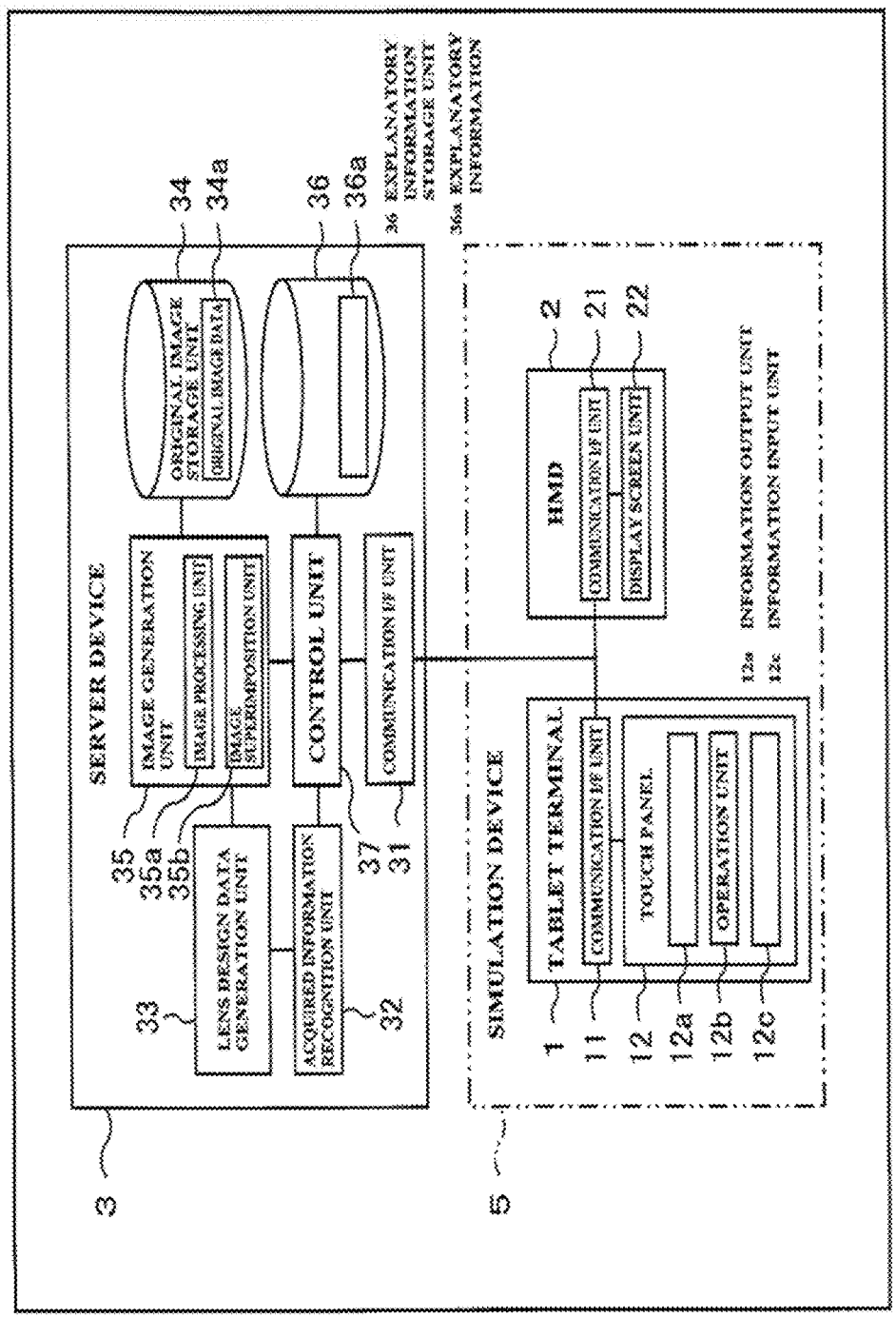
FIG. 2 is a block diagram illustrating an example of a functional configuration of a simulation system of the first embodiment of the present invention.

FIG. 2 is a block diagram illustrating an example of a functional configuration of the simulation system of the present embodiment.

In broad terms, the simulation system of the present embodiment is configured including the server device 3 and a simulation device 5. As already explained, the server device 3 and the simulation device 5 are connected together by the communication network 4 to enable communication therebetween.

Server Device

In order to give the prospective spectacle lens wearer P1 a simulation of the experience of looking through the spectacle lens, the server device 3 generates a simulation image that reflects the lens visual performance of the spectacle lens, transmits the generated simulation image to the simulation device 5, and performs other processing as required. The server device 3 is accordingly configured so as to be equipped with functions of a communication interface (interface is abbreviated to I/F below) unit 31, an acquired information recognition unit 32, a lens design data generation unit 33, an original image storage unit 34, an image generation unit 35, an explanatory information storage unit 36, and a control unit 37.

The communication I/F unit 31 implements functionality for performing communication with the simulation device 5 on the spectacle shop S side over the communication network 4.

The acquired information recognition unit 32 implements functionality for recognizing information acquired from the spectacle shop S side, through the communication I/F unit 31. The information from the spectacle shop S side includes parameter information regarding the spectacle lens the prospective spectacle lens wearer P1 is scheduled to wear. The parameter information is information regarding parameters derived from, for example, prescription information of the spectacle lens the prospective spectacle lens wearer P1 is scheduled to wear, shape information of the spectacle frame for holding the spectacle lens, and living environment information envisaged by the prospective spectacle lens wearer P1.

The lens design data generation unit 33 implements functionality to identify the sort of lens design standard that should be applied to the spectacle lens the prospective spectacle lens wearer P1 is scheduled to wear, based on the parameter information recognized by the acquired information recognition unit 32, and to generate lens design data for the spectacle lens while applying the identified sort of lens design standard. Various items are present in the sort of lens design standard to be applied, and so combinations lead to there being several hundreds of sorts of design type of the lens design data. Details of lens design standards and lens design data generation are based on known technology (see, for example, WO 2009/133887), and so explanation thereof is omitted here.

The original image storage unit 34 implements functionality for storing and retaining original image data 34a required to generate a simulation image in the image generation unit 35. An example of the original image data 34a stored and retained by the original image storage unit 34 is image data for a three dimensional computer graphic (CG) image corresponding to the original image of the simulation image. The original image is not necessarily a CG image, and, for example, may be an image captured by an imaging camera.

The original image storage unit 34 stores and retains, as the original image data 34a, image data of the original image for plural partial visual field areas that configure the full visual field area of the spectacle lens. However, as long as image data of the original image is stored and retained for at least plural partial visual field areas, the original image storage unit 34 may also store and retain other image data.

Reference here to the "full visual field area" of the spectacle lens means an area equivalent to the full visual field when looking through the spectacle lens. "Full visual field" means a range of visual field angle visible through the spectacle lens, for example, a range of about 90° in the horizontal direction, and about 70° in the vertical direction.

The plural "partial visual field areas" constituting the full visual field area are respective areas arising when the full visual field area is segmented according to a preset segmentation mode. The segmenting into each of the partial visual field areas may be performed in consideration of differences in the characteristics of lens visual performance of the spectacle lenses. As a specific example, when the spectacle lens is a progressive addition lens, for example, the full visual field area may be segmented into nine areas belonging to separate respective areas of a right side portion, a central portion, and a left side portion of a far vision area, a right side portion, a central portion, and a left side portion of a near vision area, and a right side portion, a central portion, and a left side portion of an intermediate vision area. However, it is sufficient that the plural partial visual field areas each correspond to one portion of the full visual field area, and each of the partial visual field areas may include mutually overlapping image portions.

By storing and retaining respective image data for such plural partial visual field areas, the original image storage unit 34 does not perform image output all at once for the full visual field area of the spectacle lens, and is capable of performing image output separately for each of the partial visual field areas of the full visual field area segmented into plural small visual fields The image generation unit 35 generates a simulation image that reflects the lens visual performance of the spectacle lens that the prospective spectacle lens wearer P1 is scheduled to wear. The image generation unit 35 therefore includes functionality of an image processing unit 35a and of an image superimposition unit 35b.

Based on the lens design data generated by the lens design data generation unit 33, the image processing unit 35a implements a function of performing image processing so that the visual performance (blur, distortion, etc.) identified by the lens design data is reflected in the original image data 34a stored and retained in the original image storage unit 34. This image processing generates a simulation image in which the lens visual performance of the spectacle lens the prospective spectacle lens wearer P1 is scheduled to wear is reflected in the original image for each of the partial visual field areas. Details regarding simulation image generation by image processing are based on known technology (see, for example, WO 2010/044383), and explanation thereof is omitted here.

Based on the lens design data generated by the lens design data generation unit 33, the image superimposition unit 35b implements a function to derive a clearness index of the spectacle lens the prospective spectacle lens wearer P1 is scheduled to wear, to generate an image expressing contour lines of the clearness index, and to superimpose the contour line image on the simulation image obtained by the image processing in the image processing unit 35a. The "clearness index" referred to here is one indicator for evaluating the performance of spectacle lenses (and in particular progressive addition lenses). Note that details of clarity indices are based on known technology (see, for example, Japanese Patent 3919097), and explanation thereof is omitted here.

The explanatory information storage unit 36 implements functionality to store and retain explanatory information 36a to explain the characteristics of the lens visual performance of the spectacle lens. In the explanatory information storage unit 36, due to the lens visual performance being different for each of the spectacle lens design types, storage and retention of the explanatory information 36a is performed separately for each sort of lens design standard applied to the lens design data. Moreover, due to the lens visual performance also being different for each of the respective partial visual field areas subject to image processing by the image processing unit 35a, the explanatory information 36a related to characteristics of the lens visual performance for each of the respective partial visual field areas is stored and retained associated with the respective partial visual field areas. Details and specific examples of the explanatory information 36a are given below.

The control unit 37 implements a function to perform operation control on the server device 3 as a whole. Thus operation of each of the above units 31 to 36 is controlled by the control unit 37.

Functionality as each of the units 31 to 37 is implemented by using hardware resource included in the server device 3, serving as a computer, and the server device 3 executing specific software programs. In such cases, the software programs are installed for use on the server device 3; however, there is no limitation thereto, and the software programs may be present on another device on the communication network 4 as long as they are accessible to the server device 3.

Simulation Device

The simulation device 5 is utilized on the spectacle shop S side to give the prospective spectacle lens wearer P1 the simulated experience of what it is like to look through the spectacle lens, and is specifically configured by the HMD 2 and the tablet terminal 1.

HMD

The HMD 2 performs display-output of a simulation image, in a state mounted to the head of the prospective spectacle lens wearer P1 who has visited the spectacle shop S, and thereby gives the prospective spectacle lens wearer P1 the simulated experience of what it is like to look through the spectacle lens. Thus the HMD 2 is configured with functions of a communication I/F unit 21 and of a display screen unit 22.

The communication I/F unit 21 implements a function to perform communication with the tablet terminal 1 over a wireless or wired communication line, not illustrated in the drawings. The communication I/F unit 21 may also have a combined function to perform communication with the server device 3 over the communication network 4.

The display screen unit 22 implements a function to display the simulation image generated by the server device 3 to let the prospective spectacle lens wearer P1 check the simulation image by sight. The display screen unit 22 selectively performs display of the simulation image separately for each of the partial visual field areas as the subject of image processing by the image processing unit 35a of the image generation unit 35, and also performs display of the simulation image such that the contour line image of the clearness index of the spectacle lens, from the image superimposition unit 35b of the image generation unit 35, is in a superimposed state. The display screen unit 22 is a function of the HMD 2, and so image display for each of the partial visual field areas is performed separately for the left eye and the right eye of the prospective spectacle lens wearer P1. The display screen unit 22 performs image display separately for each of the partial visual field areas, and so there is no need for the displayable image size to correspond to the full visual field area, and it may, for example, correspond to a visual field angle of about 50° in the diagonal direction of the display screen.

Tablet Terminal

The tablet terminal 1 is carried and operated by the member of staff P2 of the spectacle shop S, and is used for input and output of information required to give the prospective spectacle lens wearer P1 the simulated experience of what it is like to look through the spectacle lens. The tablet terminal 1 is accordingly configured including functions of a communication I/F unit 11 and a touch panel 12.

The communication I/F unit 11 implements functionality for performing communication with the server device 3 over the communication network 4, and also for performing communication with the HMD 2 over a wireless or wired communication line, not illustrated in the drawings.

The touch panel 12 performs information input and output, and more specifically implements functions of an information output unit 12a, an operation unit 12b, and an information input unit 12c.

The information output unit 12a implements functionality for utilizing the information output function of the touch panel 12 for display-output of various information to the member of staff P2. The various information of the information output unit 12a display-output includes the explanatory information 36a stored and retained by the explanatory information storage unit 36 of the server device 3. Namely, the information output unit 12a includes a function to acquire from the explanatory information storage unit 36 the explanatory information 36a within the explanatory information storage unit 36, and to display-output to the member of staff P2. The information output unit 12a performs display-output for the explanatory information 36a corresponding to the partial visual field area being displayed on the display screen unit 22 of the HMD 2.

The operation unit 12b implements functionality to utilize the information input function of the touch panel 12 and to perform selection operation of the partial visual field area for display on the display screen unit 22 of the HMD 2.

The information input unit 12c implements functionality to utilize the information input function of the touch panel 12 to input parameter information for the spectacle lens the prospective spectacle lens wearer P1 is scheduled to wear.

3. Procedure of Simulation Processing in Spectacle Shop

Explanation next follows regarding a procedure of simulation processing performed using the simulation system configured as described above to let the prospective spectacle lens wearer P1 experience a simulation of a lens wearing state.

Outline of Simulation Processing

First a simple outline explanation follows regarding the simulation processing performed in the spectacle shop S.

Figure 3:
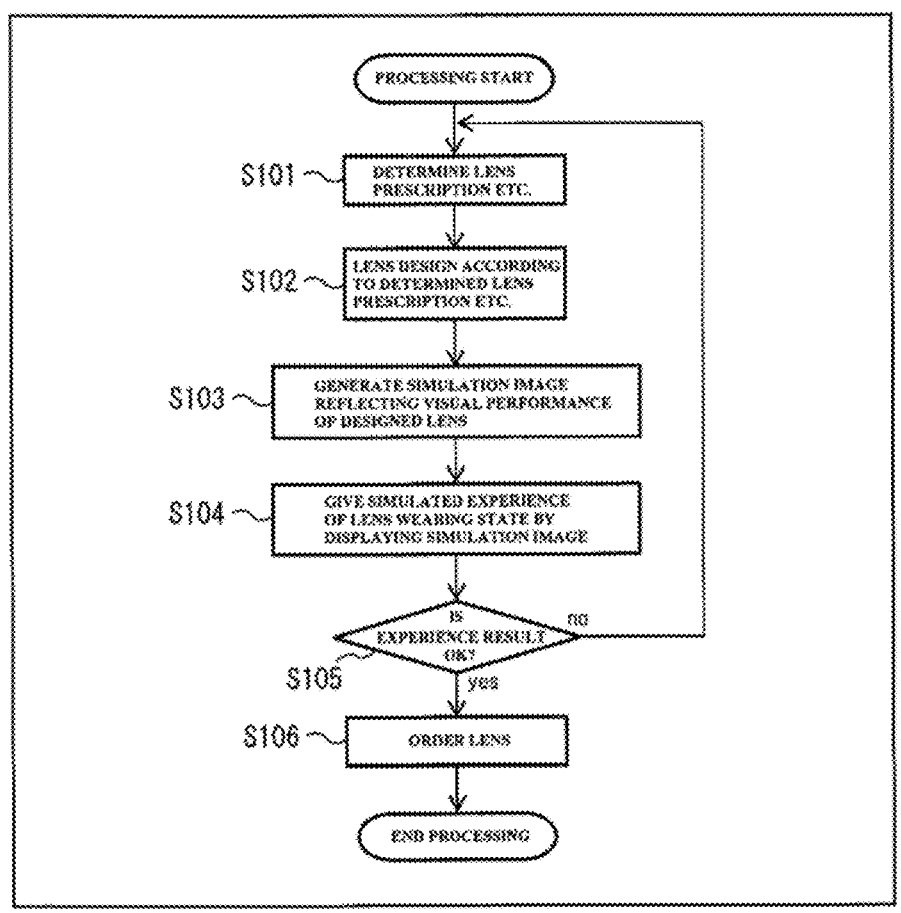
FIG. 3 is a flowchart schematically illustrating simulation processing of the first embodiment of the present invention.

FIG. 3 is a flowchart illustrating an outline of the simulation processing in the present embodiment.

In the spectacle shop S, when a prescription or the like is determined for the spectacle lens the prospective spectacle lens wearer P1 is scheduled to wear, the member of staff P2 inputs the parameter information including the prescription information using the information input unit 12c of the tablet terminal 1 (step 101, in the following step is abbreviated to "S"), and the parameter information is transmitted from the communication I/F unit 11 of the tablet terminal 1 over the communication network 4 to the server device 3.

When the transmitted parameter information arrives, the parameter information is received in the server device 3 by the communication I/F unit 31 and recognized by the acquired information recognition unit 32. The sort of lens design standard to be applied to the lens design data generation unit 33 is identified based on the recognition result, and, while applying the identified sort of lens design data, lens design data is generated for the spectacle lens the prospective spectacle lens wearer P1 is scheduled to wear (namely the spectacle lens corresponding to the determined prescription) (S102).

When the lens design data generation unit 33 has generated the lens design data, a simulation image that reflects the lens visual performance identified by the lens design data is generated by the image generation unit 35 in the server device 3 (S103). Image data for the generated simulation image is then transmitted from the communication I/F unit 31 to the spectacle shop S side over the communication network 4.

At the spectacle shop S side, the image data from the server device 3 is received by the communication I/F unit 11 of the tablet terminal 1, and, under management by the tablet terminal 1, the image data is transmitted from the communication I/F unit 11 of the tablet terminal 1 to the HMD 2, so as to be received by the communication I/F unit 21 of the HMD 2. Accordingly, under management of the tablet terminal 1, the HMD 2 displays the simulation image generated by the server device 3 on the display screen unit 22 so as to let the prospective spectacle lens wearer P1 check the simulation image by sight, and to let the prospective spectacle lens wearer P1 experience a simulation of a lens wearing state (S104).

When, as a result of checking the simulation image by sight there is no feeling of discomfort in the way the simulation image looks, and the prospective spectacle lens wearer P1 determines the result of the lens wearing state simulated experience to be OK (S105), a lens order for the prospective spectacle lens wearer P1 is made at the spectacle shop S for the determined prescription or the like (S106).

However, if the prospective spectacle lens wearer P1 has determined that the result of the lens wearing state simulated experience is no good (S105), the procedure sequence described above is repeated again after changing the prescription or the like for the spectacle lens (S101 to S105), until the result of the simulated experience is OK.

Simulation processing is thereby performed in a procedure such as that described above so as to let the prospective spectacle lens wearer P1 experience a simulated lens wearing state.

Details of the Simulation Processing

Next, a more detailed explanation follows of the procedure described above, regarding the procedure from generating the simulation image up to display-output in the simulation processing.

Figure 4:
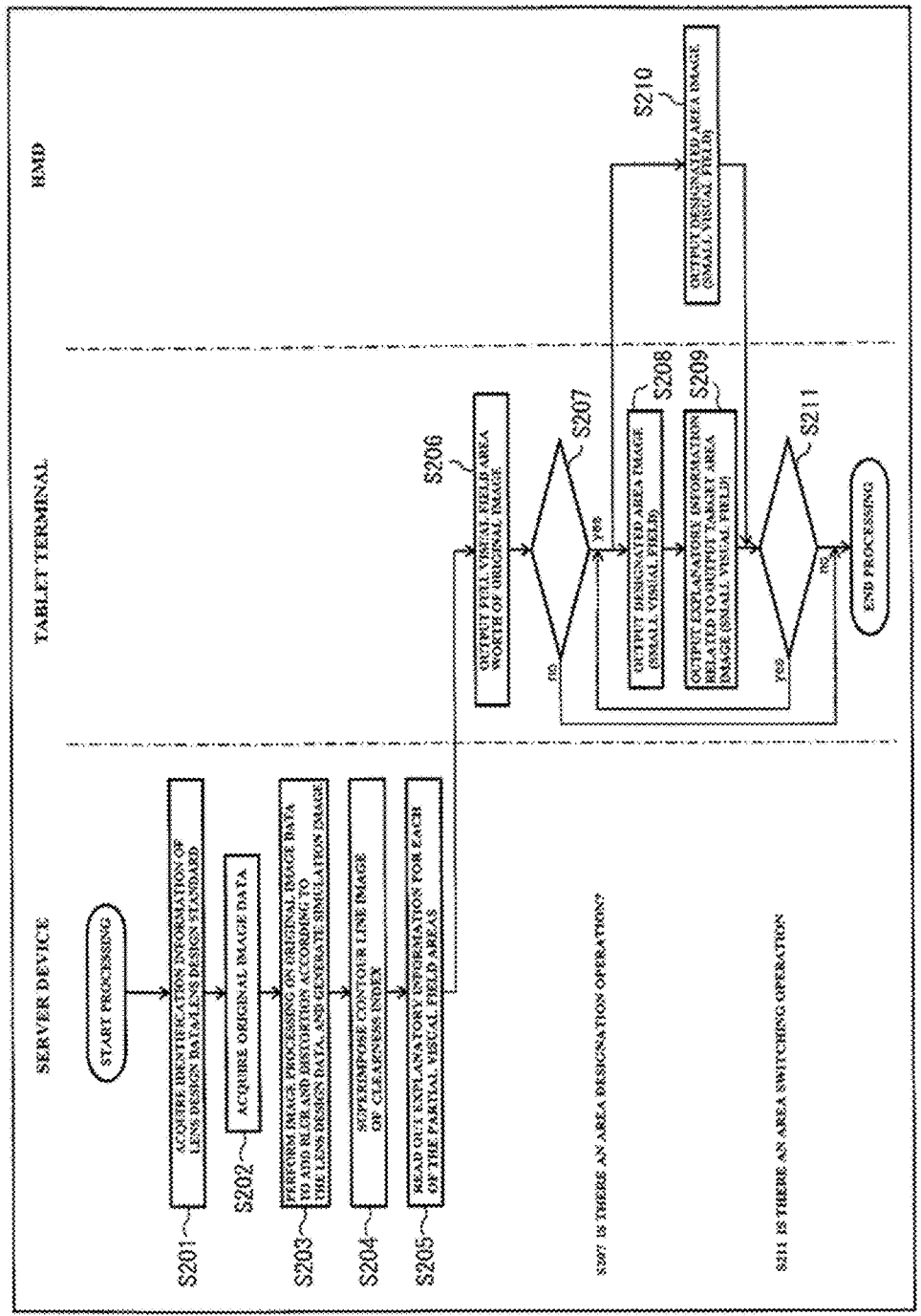
FIG. 4 is a flowchart illustrating details of a characteristic procedure of simulation processing in the first embodiment of the present invention.

FIG. 4 is a flowchart illustrating details of a characteristic procedure for simulation processing in the present embodiment.

When generating a simulation image (see S103 of FIG. 3) in the server device 3, the lens design data generated by the lens design data generation unit 33, and identification information for the sort of lens design standard applied in the lens design data generation unit 33 during this data generation, is acquired by the image generation unit 35 from the lens design data generation unit 33 (S201). Furthermore, the original image data 34a needed to generate the simulation image is acquired by the image generation unit 35 from the original image storage unit 34 (S202).

Then in the image generation unit 35, after acquiring the various data, information, etc., the image processing unit 35a generates the simulation image. Namely, the image processing unit 35a performs image processing to add blur, distortion, etc. corresponding to the acquired lens design data to the similarly acquired original image data 34a, and generates a simulation image that reflects the lens visual performance of the spectacle lens the prospective spectacle lens wearer P1 is scheduled to wear (S203). Thus, there is a state capable of outputting the simulation image not in the full visual area of the spectacle lens all at once, but in each partial visual area (namely, in each small visual area) which is obtained by dividing the full visual area into a plurality of small visual areas.

When this is performed, in the image generation unit 35 the image superimposition unit 35b generates the contour line image of the clearness index of the spectacle lens, and superimposes the contour line image on the simulation image (S204). A state is thereby obtained in which output can be performed from the server device 3 in a state in which the contour line image of the clearness index is superimposed on the partial visual field areas in the simulation image separately for each of the partial visual field areas.

Moreover, in the server device 3, when the image generation unit 35 generates the simulation image separately for each of the partial visual field areas, the control unit 37 reads the explanatory information 36a for each of the partial visual field areas from the explanatory information storage unit 36 (S205).

The control unit 37 then, as required (for example in response to a request from the tablet terminal 1) transmits image data for the simulation image separately for each of the partial visual field areas generated by the image generation unit 35 on which the contour line image has been superimposed, and transmits the explanatory information 36a read from the explanatory information storage unit 36, from the communication I/F unit 31 to the tablet terminal 1 over the communication network 4.

In the tablet terminal 1, when, for example, there is a specific operation by the member of staff P2 operating the touch panel 12, first a request is made to the server device 3 to transmit the image data for the original image of the full visual field area. In response to the request, transmitted image data for the original image of the full visual field area arrives from the server device 3. The image data at this stage may be transmitted as image data for the original image separately for all the partial visual field areas constituting the full visual field area, or, when there are overlapping image portions between each of the partial visual field areas may be transmitted after combining so as to overlap overlapping image portions. Moreover, in cases in which image data can be prepared for the original image for the full visual field area separately to the original image for each of the partial visual field areas, the image data for the full visual field area of the original image may be transmitted as it is.

When transmitted image data for the original image of the full visual field area arrives from the server device 3, the tablet terminal 1 receives the image data using the communication I/F unit 11. The information output unit 12a of the touch panel 12 then utilizes a specific portion on the display screen and performs display-output of the full visual field area worth of the sent original image (S206). The image display-output at this stage may display the original image for each of the partial visual field areas next to each other as they are, or by combining and displaying so as to overlap overlapping image portions in cases in which there are overlapping image portions present between each of the partial visual field areas.

By seeing the display-output result for the full visual field area worth of the original image, the member of staff P2 is able to appreciate the overall impression of the original image of the simulation image to be checked by sight by the prospective spectacle lens wearer P1. Details regarding the display-output mode of the full visual field area worth of the original image at this stage (including the positions of specific portions for display-output on the screen etc.) are described below (see, for example, FIG. 5).

The tablet terminal 1 determines which of the partial visual field areas has been selected and designated from out of the full visual field area worth of the original image, by the member of staff P2 performing an operation on the operation unit 12b of the touch panel 12 (S207). Specifically, for example, the presence or absence of an area designation operation is determined by whether or not one of the partial visual field areas constituting the full visual field area has been touch-operated on by the member of staff P2 in the full visual field area worth of the original image being display-output by the information output unit 12a.

When there is an area designation operation using the operation unit 12b of the touch panel 12, in the tablet terminal 1, a request to transmit the image data for the selected and designated partial visual field area (namely the small visual field worth) of the simulation image, and the explanatory information 36a for the partial visual field area, is sent to the server device 3, and a transmission arriving in response is received by the communication I/F unit 11. Then in the tablet terminal 1, separately to the full visual field area of the original image, the information output unit 12a of the touch panel 12 utilizes a specific portion on the display screen to expand the selected and designated partial visual field area (namely the small visual field worth) of the simulation image onto which the contour line image has been superimposed (referred to below as "the small visual field worth of simulation image") by expansion of more than the display of the original image, and to perform display-output (S208). In the tablet terminal 1, separately to the full visual field area worth of the original image and the small visual field worth of the simulation image, the information output unit 12a of the touch panel 12 utilizes a specific portion on the display screen to output and display the explanatory information 36a related to the selected and designated partial visual field area (namely the small visual field worth) (S209). Specific details regarding the display-output mode of the small visual field worth of the simulation image and the explanatory information 36a (including the position of the specific portions for display-output on the screen, etc.) is described later (see, for example, FIG. 5).

When there is an area designation operation using the operation unit 12b of the touch panel 12, separately to display-output and the like by the touch panel 12 as described above, the tablet terminal 1 also transmits image data for the small visual field worth of the simulation image from the communication I/F unit 11 to the HMD 2.

Transmitted image data for the small visual field worth of the simulation image arriving from the tablet terminal 1 is received in the HMD 2 by the communication I/F unit 21. The display screen unit 22 of the HMD 2 then performs display-output of the sent small visual field worth of the simulation image (S210). The image display-output is performed separately for the left eye and right eye of the prospective spectacle lens wearer P1. This thereby enables what is referred to as 3D display to be performed for the prospective spectacle lens wearer P1. Showing such a display-output result gives the prospective spectacle lens wearer P1 the simulated experience of a lens wearing state.

The image display-output of the display screen unit 22 at this time is for the small visual field worth, rather than for the full visual field area worth, of the simulation image. Thus even in cases in which the display screen unit 22 is only capable of handling a visual field angle of about 50° in the diagonal direction, compared to a full visual field area through the spectacle lens of, for example, about 90° in the horizontal direction and about 70° in the vertical direction, the display screen unit 22 is able to perform image display-output without needing to shrink the simulation image or the like.

Thus at the spectacle shop S side, the HMD 2 lets the prospective spectacle lens wearer P1 check the small visual field worth of the simulation image by sight to give the prospective spectacle lens wearer P1 the simulated experience of the lens wearing state, and the explanatory information 36a corresponding to the small visual field worth (the partial visual field area) being display-output by the HMD 2 is display-output on the tablet terminal 1 for the member of staff P2. The member of staff P2 is accordingly able to accurately recognize the characteristics of the lens visual performance by referring to the display-output result of the explanatory information 36a, even without completely memorizing the lens visual performance of the small visual field worth (the partial visual field area). The member of staff P2 reading out the display-output result of the explanatory information 36a, and notifying the display-output result to the prospective spectacle lens wearer P1, enables the prospective spectacle lens wearer P1 to be made sufficiently aware of the characteristics of the lens visual performance. Namely, by utilizing the display-output result of the explanatory information 36a on the tablet terminal 1, the prospective spectacle lens wearer P1 is able to be made appropriately and sufficiently aware of the characteristics of the lens visual performance of the spectacle lens selected by the prospective spectacle lens wearer P1, using accurate information based on the explanatory information 36a, rather than ambiguous information based on the memory of the member of staff P2.

Then the tablet terminal 1 determines whether or not another partial visual field area has been selected and designated from out of the full visual field area worth of the original image, namely whether or not there has been an operation to switch the selected and designated partial visual field area (S211). Specifically, for example, determination is made as to whether or not an area switching operation to a different partial visual field area has been made to the full visual field area worth of the original image being output and displayed by the information output unit 12a, to the small visual field worth (partial visual field area) being display-output on the HMD 2, by whether or not a touch-operation has been made on the operation unit 12b of the touch panel 12 by the member of staff P2.

When there has been an area switching operation using the operation unit 12b of the touch panel 12, the procedure sequence described above is repeated again in the tablet terminal 1 and the HMD 2 for the partial visual field area (namely the small visual field worth) newly selected and designated in the tablet terminal 1 by the switching operation (S208 to S211).

Then when there is no area designation operation or area switching operation with the operation unit 12b of the touch panel 12, the server device 3, the tablet terminal 1, and the HMD 2 end one sequence of the processing to generate and display-output the simulation image as described above, and get the prospective spectacle lens wearer P1 to determine the result of the simulated experience of the lens wearing state (see S104 of FIG. 3).

Spectacle Shop Product Explanation Assistance Method

In the spectacle shop S, the simulation system performing a simulation processing procedure such as that described above assists explanation regarding the spectacle lens to the prospective spectacle lens wearer P1 by the member of staff P2. Namely, in the spectacle shop S, the simulation system assists explanation by the member of staff P2 of the spectacle shop S by progressing in sequence through an image display step, in which a simulation image is selectively shown to the prospective spectacle lens wearer P1 separately for each of the partial visual field areas with the HMD 2, an information output step, in which the explanatory information 36a corresponding to the partial visual field area being display-output on the HMD 2 is output utilizing the tablet terminal 1, and a selection switching step of switching the selection of the partial visual field area being displayed by the HMD 2 and performing corresponding switching of the explanatory information 36a output by the tablet terminal 1.

Specific Example of Display-Output Content of Tablet Terminal

Detailed explanation follows regarding a specific example of content of display-output performed by the touch panel 12 of the tablet terminal 1 in the simulation processing of the procedure described above.

Figure 5:
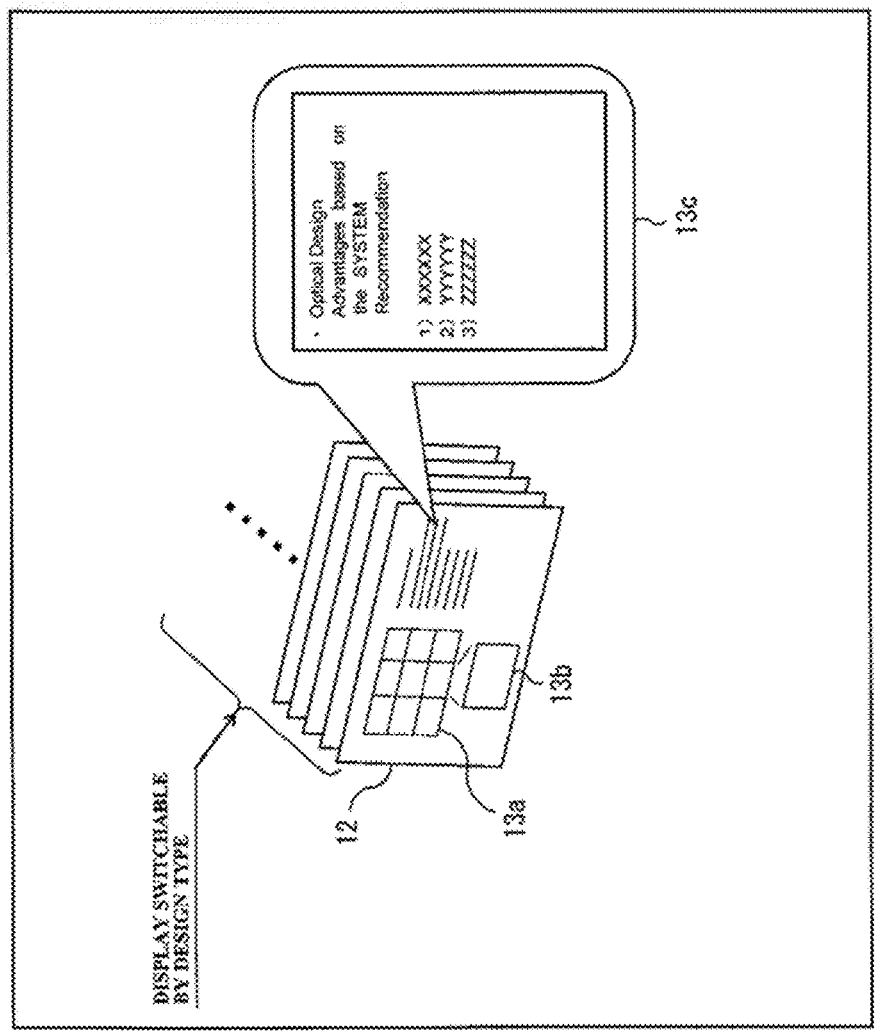
FIG. 5 is a schematic diagram illustrating a specific example of display-output content by a tablet terminal of the first embodiment of the present invention.

FIG. 5 is a schematic diagram illustrating a specific example of display-output content on the tablet terminal in the present embodiment.

On the display screen of the touch panel 12, the full visual field area worth of an original image 13a is display-output on a part region, for example at the top left of the screen. This original image 13a is an example for a case in which each of the partial visual field areas that have been segmented into nine areas are display-output next to each other in a three row and three column pattern to as to recreate a state prior to being segmented.

On the display screen of the touch panel 12, for example at a part region below the display region of the full visual field area worth of the original image 13a (namely at the bottom left of the screen), a partial visual field area selected and designated in the full visual field area worth of the original image 13a is display-output in an expanded state as the small visual field worth of the simulation image 13b. The small visual field worth of the simulation image 13b being display-output is that which has been selected and designated by the member of staff P2, and is that which is being display-output on the display screen unit 22 of the HMD 2. The member of staff P2 is accordingly able to appropriately and easily ascertain which partial visual field area is being display-output by the display screen unit 22 of the HMD 2 by referring to the small visual field worth of the simulation image 13b being display-output. Moreover, superimposing the contour line image of the clearness index on the small visual field worth of the simulation image 13b enables the characteristics of the lens visual performance to be easily and clearly ascertained.

Moreover, on the display screen of the touch panel 12, for example in a part region on the right of the screen, a text image 13c is display-output for the explanatory information corresponding to the partial visual field area selected and designated in the full visual field area worth of the original image 13a. The text image 13c for the explanatory information being display-output here is an image representing text to explain the characteristics of the lens visual performance for the partial visual field area being display-output as the small visual field worth of the simulation image 13b. Specifically, for example, text such as "portion a has characteristic x", and "portion b has a wide application range of y" etc., is displayed and output as the text image 13c for the explanatory information. This thereby enables the member of staff P2 to accurately confirm what characteristics the lens visual performance has for the partial visual field area being display-output on the display screen unit 22 of the HMD 2 by referring to the text image 13c for the explanatory information being display-output.

The small visual field worth of the simulation image 13b and the text image 13c for the explanatory information corresponding thereto in the display-output contents switch according to touch-operation employed on the full visual field area worth of the original image 13a. For example, when touch-operation is performed on one partial visual field area in the full visual field area worth of the original image 13a, the corresponding small visual field worth of simulation image 13b and the text image 13c for the explanatory information is display-output; however, when this is followed by touch-operation of another partial visual field area, the display-output content is switched that of the corresponding small visual field worth of the simulation image 13b, and of the text image 13c for the explanatory information. Namely, the small visual field worth of the simulation image 13b and the text image 13c for the explanatory information is selectively display-output separately for each of the partial visual field areas.

Such display-output content also differs by spectacle lens design type. Namely, if the sort of lens design standard applied by the lens design data generation unit 33 is different, then the generation result of the simulation image performed by the image processing unit 35*a* based on the lens design data generated by the lens design data generation unit 33 also differs. Thus the full visual field area worth of a different original image 13*a*, and the corresponding small visual field worth of the simulation image 13*b* and the text image 13*c* for the explanatory information, are display-output by spectacle lens design type on the display screen of the touch panel 12. This means that the display screen of the touch panel 12 is able to perform display switching by spectacle lens design type.

The output layout on the display screen in this example is merely a specific example thereof. Namely, the output layout on the display screen of the touch panel 12 is not particularly limited as long as it is set in advance as appropriate.

Specific Example of Display-Output Content on HMD

Detailed explanation follows regarding a specific example of content of display-output performed by the display screen unit 22 of the HMD 2 in the simulation processing of the procedure described above.

Figure 6:
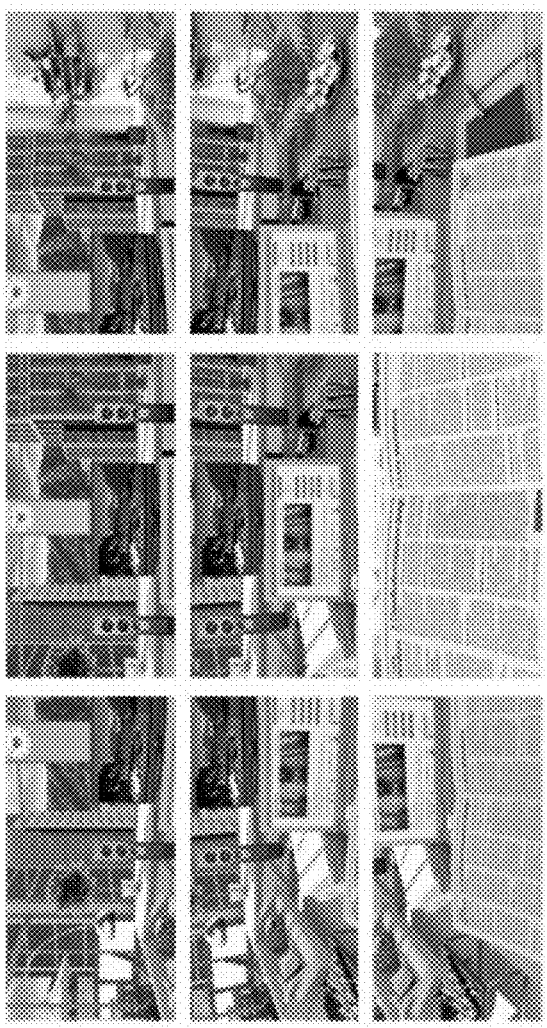
FIG. 6 is an explanatory diagram of images handled in simulation processing in the first embodiment of the present invention and illustrating a specific example of original images that are the basis of simulation image generation.

FIG. 6 is an explanatory diagram illustrating a specific example of an original image that is the basis for simulation image generation.

The original image in the illustrated example is the full visual field area of the spectacle lens segmented into nine partial visual field areas (small visual fields). When the spectacle lens is a progressive addition lens, the segmentation results in a right side portion, a central portion, and a left side portion of a far vision area, a right side portion, a central portion, and a left side portion of a near vision area, and a right side portion, a central portion, and a left side portion of an intermediate vision area, respectively belonging to separate partial visual field areas. Each of the partial visual field areas includes an image portion that overlaps with an adjacent partial visual field area. The original image for the central portion of the near vision area is envisaged as paper carrying text that is held up and read by the prospective spectacle lens wearer P1.

Figure 7:
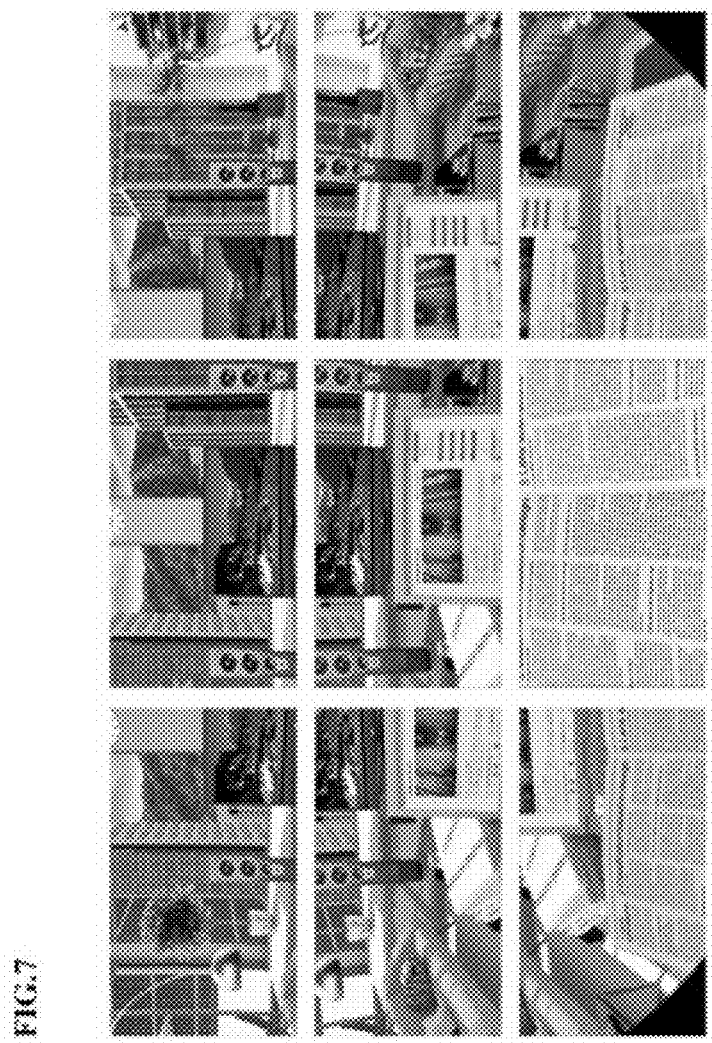
FIG. 7 is an explanatory diagram of images handled in simulation processing in the first embodiment of the present invention and illustrating a specific example of simulation images obtained by performing image processing on an original image.

FIG. 7 is an explanatory diagram illustrating a specific example of simulation images obtained by performing image processing on the original image.

The simulation images of the illustrated example are those obtained by performing image processing on the respective original images separately for the partial visual field areas illustrated in FIG. 6. The image processing reflects for example, the lens visual performance of a progressive addition lens for the right eye with a spherical diopter S of 2.00, a cylindrical diopter C of −1.00, a cylindrical axis Ax of 180, an addition Add of 2.50, a progressive zone length of 14 mm, and a pupillary distance PD=32+32 mm.

Figure 8:
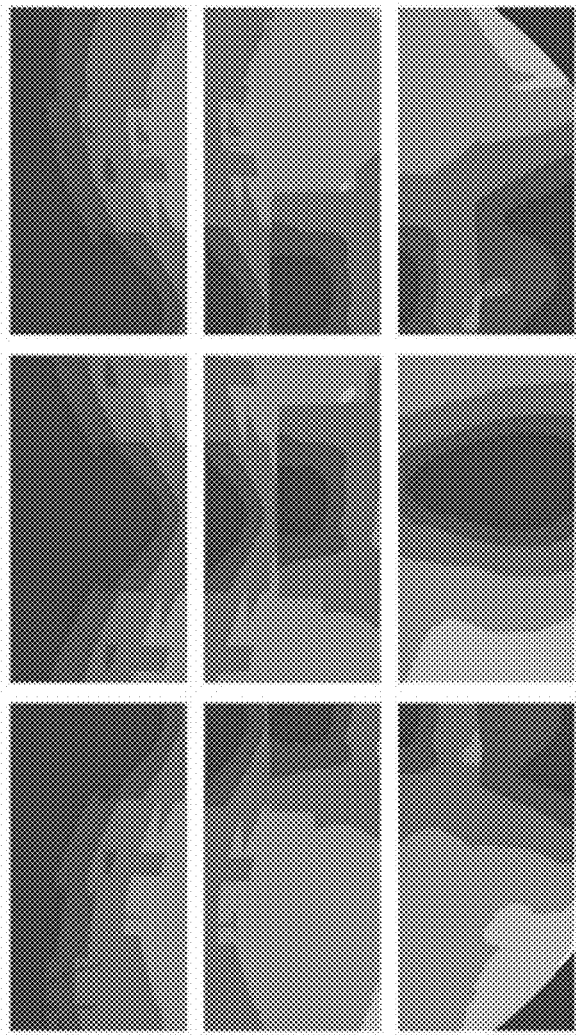
FIG. 8 is an explanatory diagram of images handled in simulation processing in the first embodiment of the present invention and illustrating a specific example of images showing contour lines of a clearness index of a spectacle lens.

FIG. 8 is an explanatory diagram illustrating a specific example of image showing contour lines of a spectacle lens clearness index.

The contour line images in the illustrated example corresponds to the segmented original image separately for the partial visual field areas illustrated in FIG. 6, and so are images with different display brightness according to the clearness index of the spectacle lens. Boundary portions between area portions having the same display brightness and adjacent area portions having another display brightness correspond to clearness index contour lines. The spectacle lens, similarly to in FIG. 7, envisages a progressive addition lens for the right eye with a spherical diopter S of 2.00, a cylindrical diopter C of −1.00, a cylindrical axis Ax of 180, an addition Add of 2.50, a progressive zone length of 14 mm, and a pupillary distance PD=32+32 mm.

Figure 9:
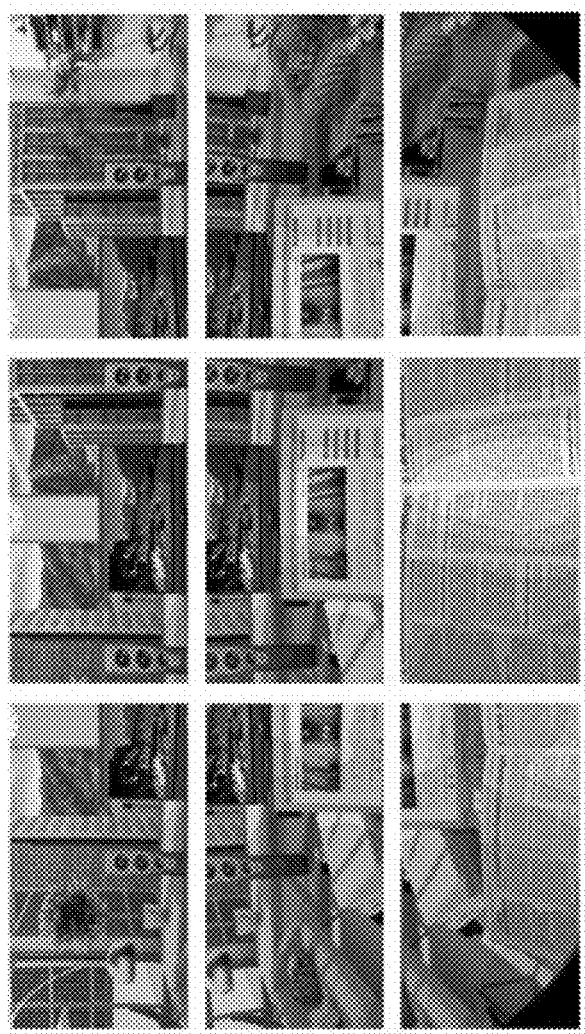
FIG. 9 is an explanatory diagram of images handled in simulation processing in the first embodiment of the present invention and illustrating a specific example of simulation images superimposed with contour line images of a clearness index separately for partial visual field areas.

FIG. 9 is an explanatory diagram illustrating a specific example of simulation images separate for partial visual field areas with contour line images of the clearness index superimposed.

The image in the illustrated example is one in which the contour line images of FIG. 8 have been superimposed on the simulation images of FIG. 7. The brightness of the images has been adjusted according to the values of the clearness index. The display screen unit 22 of the HMD 2 selectively outputs and displays such simulation images with the contour line images superimposed separately for each of the partial visual field areas.

4. Advantageous Effects of Present Embodiment

The following advantageous effects are obtained by the present embodiment.

In the present embodiment, while giving the prospective spectacle lens wearer P1 a simulation of the experience of a lens wearing state, the explanatory information 36*a* corresponding to the small visual field worth (partial visual field area) being display-output on the display screen unit 22 of the HMD 2 is display-output to the member of staff P2 by the information output unit 12*a* of the tablet terminal 1. Namely, explanatory information 36*a* related to characteristics of the lens visual performance is pre-prepared by design type and separately for each of the partial visual field areas, and output of the explanatory information 36*a* corresponding to the display content is performed to match display of the simulation images to the prospective spectacle lens wearer P1. The member of staff P2 is thereby able to accurately confirm the characteristics of the lens visual performance by referencing the display-output result of the explanatory information 36*a*, even without completely memorizing the lens visual performance of the small visual field worth (the partial visual field area). Moreover, the member of staff P2 reading out the display-output result of the explanatory information 36*a*, and notifying the display-output result to the prospective spectacle lens wearer P1, also enables the prospective spectacle lens wearer P1 to be made sufficiently aware of the characteristics of the lens visual performance.

Thus, according to the present embodiment, even in cases in which there are several hundred sorts of characteristics of lens visual performance for each spectacle lens according to design type and so on, such as, for example, in a progressive addition lens having a free curved surface of individual design, on top of the prospective spectacle lens wearer P1 being able to be made sufficiently aware of the differences in characteristics of the lens visual performance irrespective of the skills and the like of the member of staff P2, the prospective spectacle lens wearer P1 can be made to determine the appropriateness or otherwise of the result of the simulated experience, enabling the prospective spectacle lens wearer P1 to be given a feeling of satisfaction.

Moreover, in the present embodiment, while giving the prospective spectacle lens wearer P1 the simulated experience of a lens wearing state, the simulation image is selectively displayed by the display screen unit 22 of the HMD 2 separately by small visual field worth (partial visual field area), to get the prospective spectacle lens wearer P1 to check by sight. Namely, display of the simulation images is selectively performed separately for plural partial visual field areas constituting the full visual field area, rather than being performed for the full visual field area of the spectacle lens all at once. Thus even in cases in which the display screen unit 22 has a visual field angle of about 50° in the diagonal direction, compared to the full visual field area through the spectacle lens of about 90° in the horizontal direction and about 70° in the vertical direction, the display screen unit 22 is able to perform image display-output without needing to shrink the simulation image or the like. Moreover, even in cases in which display of the simulation images is performed for each of the small visual field worth (the partial visual field areas), switching the selected area makes it still possible to get the prospective spectacle lens wearer P1 to clearly check the full visual field worth of the spectacle lens by sight.

The present embodiment thereby enables the prospective spectacle lens wearer P1 to be given the simulated experience of a lens wearing state by using the compact and low cost HMD 2, without needing to be able to regenerate the full visual field area of the spectacle lens all at once on the display screen unit 22. Moreover even in such cases, the prospective spectacle lens wearer P1 can be made to clearly check the full visual field area worth by sight by switching the display area, enabling any dissatisfaction that might be felt by the spectacle shop S side when the simulation device 5 is introduced to be eliminated.

Moreover, in the present embodiment, the simulation system assists product explanation to the prospective spectacle lens wearer P1 regarding the spectacle lens, by the member of staff P2. Namely, by utilizing the display-output result of the explanatory information 36a on the tablet terminal 1, the prospective spectacle lens wearer P1 is able to be made appropriately and sufficiently aware of the characteristics of the lens visual performance of the spectacle lens selected by the prospective spectacle lens wearer P1, using accurate information based on the explanatory information 36a, rather than ambiguous information based on the memory of the member of staff P2.

Thus in the present embodiment, the prospective spectacle lens wearer P1 is able to be made sufficiently aware of the characteristics of the lens visual performance of the spectacle lens without the member of staff P2 needing high skills and the like. Namely, while giving the prospective spectacle lens wearer P1 the simulated experience of a lens wearing state, any dissatisfaction felt, such as by the prospective spectacle lens wearer P1 or on the spectacle shop S side, is eliminated, so as to give a feeling of satisfaction to each respectively.

In the present embodiment, on display-output of the simulation images, display-output is performed of the simulation images with the contour lines of the clearness index of the spectacle lens superimposed thereon. This thereby enables the characteristics of the lens visual performance to be ascertained more easily than cases lacking superimposition of the contour line images. This is particularly effective in cases in which the resolution in the display screen unit 22 of the HMD 2 is not sufficient. This is because there is a concern that blur, distortion, etc. reflected in the simulation images may not be completely reproducible when there is not sufficient resolution in the display screen unit 22, however, superimposing the contour line images enables the portions that cannot be completely reproduced to be supplemented by the contour lines; a low resolution is acceptable for the display screen unit 22, enabling the prospective spectacle lens wearer P1 to be given a virtual experience of a lens wearing state by using a compact and low cost HMD 2. Furthermore, the differences in the superimposed contour line images enables subtle differences in lens visual performance between each spectacle lens to be made apparent.

In the present embodiment, display of the simulation images to the prospective spectacle lens wearer P1 is performed by employing the HMD 2 mounted to the head of the prospective spectacle lens wearer P1, and the display screen unit 22 of the HMD 2 operates separately for the left eye and right eye of the prospective spectacle lens wearer P1, respectively. Thus the present embodiment is able to give the prospective spectacle lens wearer P1 a simulated experience of a lens wearing state, while suitably accommodating the special characteristics of spectacle lenses, where it is possible that spectacle lenses to be worn on the left and right eyes differ in prescription etc. Moreover it is possible to easily accommodate what is referred to as 3D display when displaying the simulation image, enabling image display to be performed to the prospective spectacle lens wearer P1 overflowing in realism, and making it easy for the prospective spectacle lens wearer P1 to determine the result of the simulated experience. Moreover, on the spectacle shop S side, since a large scale display device is not required, and the prospective spectacle lens wearer P1 can be given the simulation of the experience of a lens wearing state using the compact and lightweight HMD 2, an advantageous increase in the effective utilization of store space etc. is achieved.

In the present embodiment, the tablet terminal 1 employed by the member of staff P2 performs display-output of the explanatory information 36a, etc. Namely, the information output unit 12a is provided in the tablet terminal 1 to perform display-output of the explanatory information 36a etc. Thus according to the present embodiment, the member of staff P2 is capable of performing product explanation of the spectacle lens to the prospective spectacle lens wearer P1 while holding the highly portable tablet terminal 1 in their hands, which is extremely convenient for the member of staff P2. The display-output of the explanatory information 36a etc. utilizes information output functions etc. that are generally provided in a tablet terminal 1, thereby enabling a general purpose configuration to be employed for the tablet terminal 1, and contributing to achieving a cost reduction in the simulation device 5.

In the present embodiment, the selection operation for the small visual field worth (the partial visual field area) to be displayed on the HMD 2 (including both the area designation operation and the area switching operation) is performed by the member of staff P2 on the tablet terminal 1. Namely, the operation unit 12b is provided to the tablet terminal 1 in order for the member of staff P2 to perform the selection operation. Thus the present embodiment enables the member of staff P2 employing the tablet terminal 1 to appropriately and easily ascertain which small visual field worth (partial visual field area) the HMD 2 is performing display-output of and makes it easy for the member of staff P2 to perform a product explanation of the spectacle lens to the prospective spectacle lens wearer P1.

In the present embodiment, the tablet terminal 1 employed on the spectacle shop S side communicates with the server device 3 over the communication network 4, and acquires the simulation image and the explanatory information 36a from the server device 3. Namely, the communication I/F unit 11 is provided in the tablet terminal 1 in order to acquire the simulation image and the explanatory information 36a, and the explanatory information storage unit 36 is provided in the server device 3 to store and retain the image generation unit 35 for generating the simulation image and the explanatory information 36a. Thus in the simulation system of the present embodiment, the simulation image generation that has a heavy processing load, and the storage and retention of the explanatory information 36a that requires a large storage capacity, are performed concentrated on the server device 3 side that has a high processing capacity, making implementation of efficient management of each resource in the system possible. Moreover, since there is no need in the tablet terminal 1 and the HMD 2 constituting the simulation device 5 employed on the spectacle shop S side for such high processing capacity as that for performing the simulation image generation etc., this enables a contribution to be obtained to a reduction in cost for building the simulation system. This is particularly effective in cases in which plural tablet terminal 1 and HMDs 2 (namely plural spectacle shops S) are connected to the server device 3.

Moreover, in the present embodiment, the tablet terminal 1 is equipped with the information input unit 12c for inputting parameter information of the spectacle lens, and the server device 3 is equipped with the lens design data generation unit 33 for generating the lens design data of the spectacle lens while identifying the sort of lens design standard that should be applied based on the parameter information. Thus the present embodiment is capable of performing processing from generation of lens design data to generation of simulation images as one processing sequence on the server device 3 side. Namely, efficiencies are achieved in processing execution on the server device 3 side. As viewed from the spectacle shop S side, transmitted simulation images etc. arrive from the server device 3 as long as parameter information etc. is input, and so there is a high convenience for both the prospective spectacle lens wearer P1 and the member of staff P2 of the spectacle shop S, respectively.

B. Second Embodiment

Explanation next follows regarding a second embodiment of the present invention.

Explanation follows regarding points of difference to the first embodiment described above.

The second embodiment to be explained differs from the first embodiment described above in the contents of the simulation images that are output by display.

Outline of Simulation Processing

Figure 10:
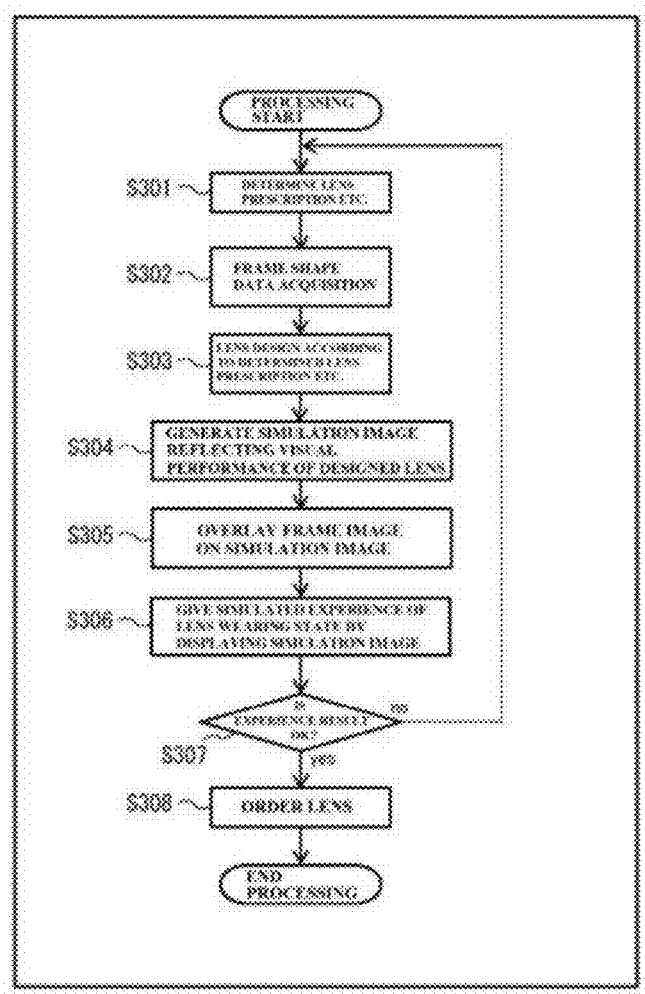
FIG. 10 is a flowchart schematically illustrating simulation processing of a second embodiment of the present invention.

FIG. 10 is a flowchart illustrating an outline of simulation processing in the second embodiment.

In the second embodiment, parameter information including prescription information of the spectacle lens the prospective spectacle lens wearer P1 is to wear, shape information of a spectacle frame for holding the spectacle lens, and the like is input to the information input unit 12c of the tablet terminal 1 (S301), and the parameter information is transmitted to the server device 3 over the communication network 4. When the transmitted parameter information arrives in the server device 3 it is received by the communication I/F unit 31, and is recognized by the acquired information recognition unit 32. The acquired information recognition unit 32 then acquires frame shape data identifying the frame shape of the spectacle frame based on the shape information of the spectacle frame included in the parameter information (S302). The lens design data generation unit 33 then, based on the recognition result of the prescription information etc. by the acquired information recognition unit 32, generates lens design data of the spectacle lens scheduled to be worn by the prospective spectacle lens wearer P1 (namely, a spectacle lens corresponding to the determined prescription etc.) (S303).

When the lens design data generation unit 33 has generated the lens design data, the image generation unit 35 in the server device 3 generates a simulation image that reflects the lens visual performance identified by the lens design data (S304). The image generation unit 35 also generates a frame image of the spectacle frame based on the frame shape data acquired by the acquired information recognition unit 32, and overlays this on the simulation image (S305). Specifically, the frame image of the spectacle frame is superimposed on the simulation image so as to be overlaid on the simulation image. The server device 3 then transmits the image data for the simulation image on which the frame image is overlaid, from the communication I/F unit 31 to the spectacle shop S side over the communication network 4.

Subsequent processing (S306 to S308) is similar to that of the first embodiment (see FIG. 3).

Details of Simulation Processing

Detailed explanation continues regarding a procedure from generating the simulation image to display-output in the simulation processing of the procedure described above.

Figure 11:
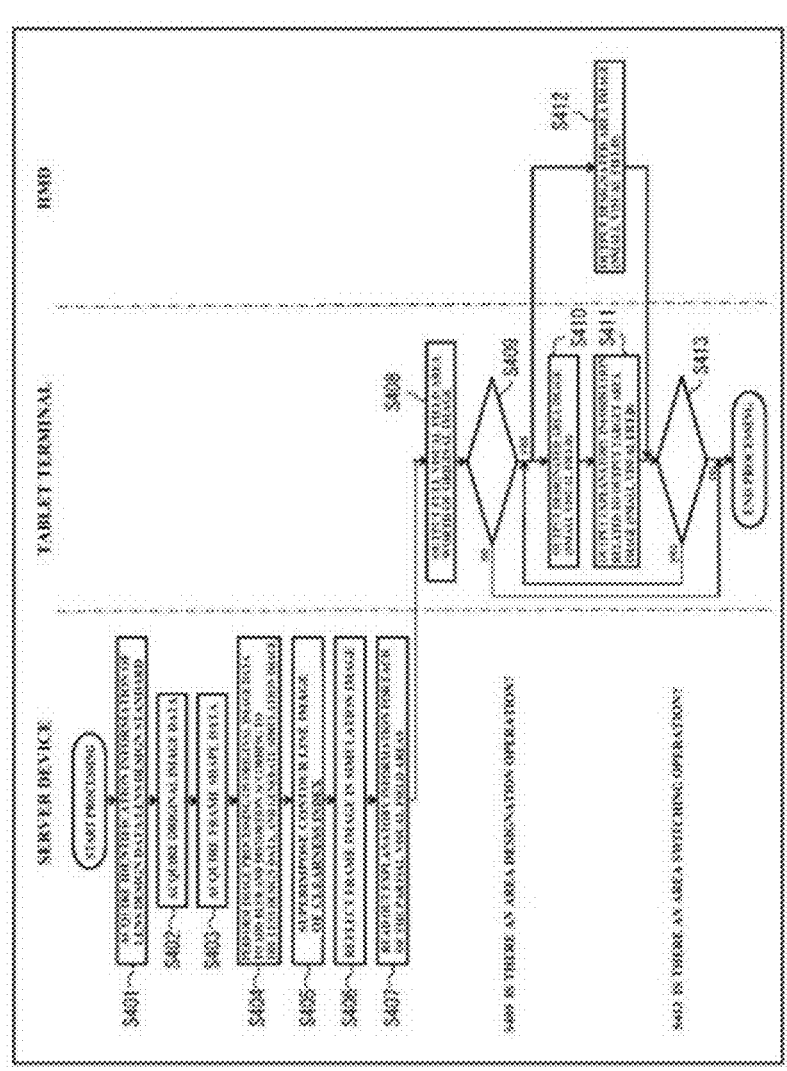
FIG. 11 is a flowchart illustrating details of a characteristic procedure of simulation processing in the second embodiment of the present invention.

FIG. 11 is a flowchart illustrating details of a characteristic procedure of the simulation processing in the second embodiment.

The image generation unit 35 of the server device 3 acquires from the lens design data generation unit 33 the lens design data generated by the lens design data generation unit 33 at generation of the simulation image (see S304, S305 in FIG. 10), and the identification information for the sort of lens design standard the lens design data generation unit 33 applied when generating the data (S401). The image generation unit 35 then acquires the original image data 34a needed for generating the simulation image from the original image storage unit 34 (S402). The image generation unit 35 also acquires the frame shape data for the spectacle frame for holding the spectacle lens from the acquired information recognition unit 32 (S403).

After acquiring the various data and information etc., the image processing unit 35a in the image generation unit 35 generates the simulation image. Namely, the image processing unit 35a performs image processing to add blur, distortion, etc. corresponding to the acquired lens design data to the likewise acquired original image data 34a, and generates a simulation image that reflects the lens visual performance of the spectacle lens scheduled to be worn by the prospective spectacle lens wearer P1 (S404). A state is thereby obtained in which simulation images can be output from the server device 3 separately for each of the partial visual field areas (namely by small visual fields) of the full visual field area segmented into plural small visual fields, rather than for the full visual field area of the spectacle lens all at once.

When this is performed, the image superimposition unit 35b in the image generation unit 35 generates contour line images of a clearness index of the spectacle lens, and superimposes the contour line images on the simulation images (S405). A state is thereby obtained in which output from the server device 3 can be performed with the contour line images of the clearness index for the partial visual field areas in a superimposed state on the simulation images separately for each of the partial visual field areas.

Moreover, when this is performed, the acquired information recognition unit 32 in the image generation unit 35 generates a frame image of the spectacle frame based on frame shape data acquired by the acquired information recognition unit 32. Overlay processing is then performed to overlay the generated frame image on the simulation image (S406). The overlay processing, for example, performed as follows may be considered. First the image generation unit 35 identifies the frame shape of the spectacle frame based on the frame shape data. The image generation unit 35 also identifies the position on the simulation image where the frame of the spectacle frame is to be disposed, utilizing the cornea-vertex distance (wear distance) prescribed for the spectacle lens scheduled to be worn by the prospective spectacle lens wearer P1. The image generation unit 35 employs these identification results to generate a frame image of the spectacle frame as it would be seen by the prospective spectacle lens wearer P1, and performs overlay processing on the simulation image by superimposing the frame image on the simulation images separately for each of the partial visual field areas. Thus, the frame image of the spectacle frame that would be seen in the partial visual filed, is overlaid on the simulation image in each partial visual field, and in this state (namely, in a superimposition state), the simulation image can be outputted.

Then in the server device 3, the control unit 37 reads the explanatory information 36a for each of the partial visual field areas from the explanatory information storage unit 36 (S407). The control unit 37 transmits the image data and the explanatory information 36a to the tablet terminal 1 via the communication network 4 from the communication I/F unit 31 as required (for example, responding to a request from the tablet 1), wherein the image data is the data regarding the simulation image in each partial visual field area generated by the image generation unit 35, with the contour line image superimposed thereon and the frame image overlaid thereon, and the explanatory information 36 is the information read from the explanatory information storage unit 36.

The following processing (S408 to S418) is similar to that of the first embodiment (see FIG. 4).

Specific Example of Display-Output Content by HMD

Detailed explanation follows regarding content for the display screen unit 22 of the HMD 2 to perform display-output in the simulation processing of the procedure described above, with specific examples given.

In the specific example that follows, the original image on which the simulation image generation is based is similar to that of the first embodiment (see FIG. 6).

Figure 12:
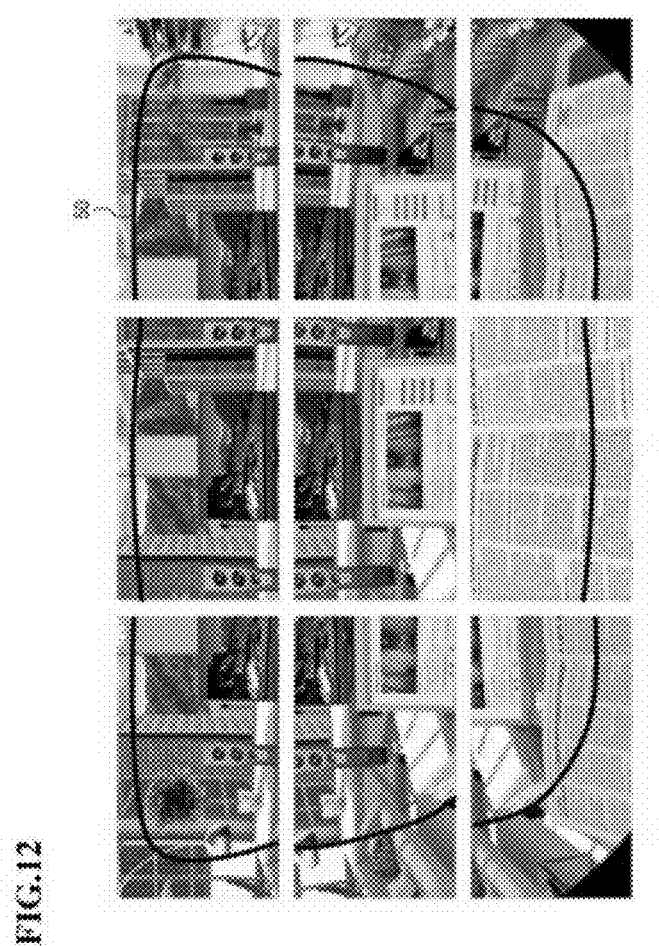
FIG. 12 is an explanatory diagram of images handled in simulation processing in the second embodiment of the present invention and illustrating a specific example in which a frame image is overlaid on simulation images obtained by performing image processing on an original image.

FIG. 12 is an explanatory diagram illustrating a specific example in which a frame image is overlaid on simulation images obtained by performing the image processing on the original image.

The simulation images of the illustrated example are obtained by performing image processing on each of the original images separately for the partial visual field areas illustrated in FIG. 6. The image processing reflects, for example, the lens visual performance of a progressive-power lens for the right eye with a spherical diopter S of 2.00, a cylindrical diopter C of −1.00, a cylindrical axis Ax of 180, an addition Add of 2.50, a progressive zone length of 14 mm, and a pupillary distance PD=32+32 mm.

Moreover, the frame image 50 corresponding to the frame of the spectacle frame, is overlaid on the simulation image in each partial visual field area in the figure. Namely, the frame image 50 is superimposed on the simulation images. Such display-output content enables the prospective spectacle lens wearer P1 who is looking at them to easily and accurately ascertain the lens visual performance of the spectacle lens (the visual performance inside the frame) in a state in which the spectacle frame is being worn (namely a state in which the frame enters the field of view).

Figure 13:
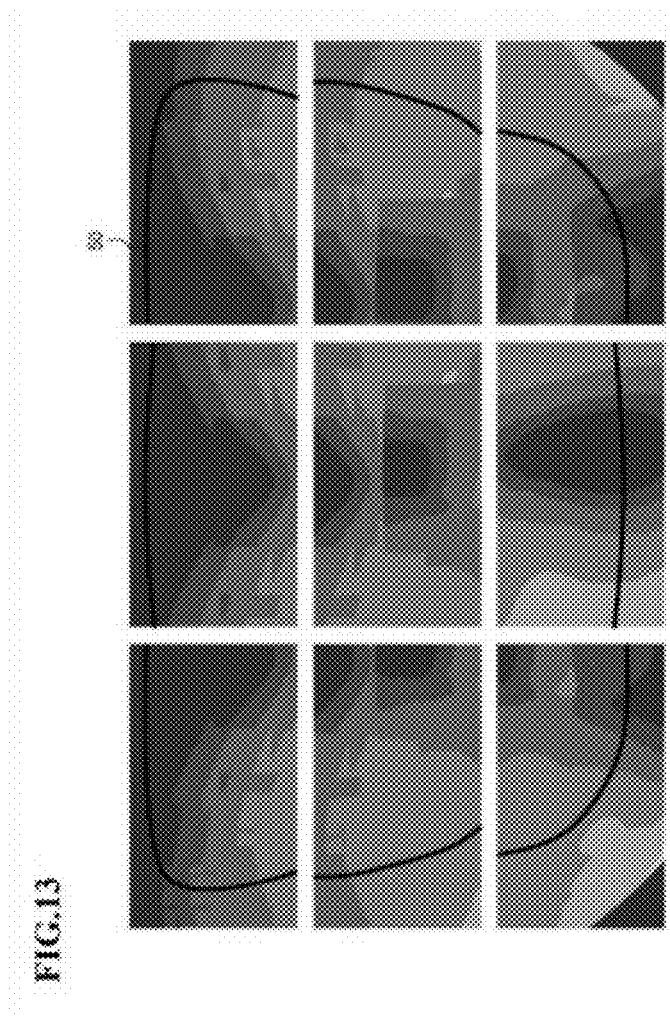
FIG. 13 is an explanatory diagram of images handled in simulation processing in the second embodiment of the present invention and illustrating a specific example in which a frame image is overlaid on images showing contour lines of a clearness index of a spectacle lens.

FIG. 13 is an explanatory diagram illustrating a specific example in which a frame image is overlaid on the images showing contour lines of a clearness index of a spectacle lens.

The contour line images of the illustrated example correspond to separate segments of the original image for the partial visual field areas illustrated in FIG. 6, and are images imparted with different display brightness according to the clearness index of the spectacle lens. Boundary portions between area portions having the same display brightness and adjacent area portions having another display brightness correspond to clearness index contour lines. The spectacle lens, similarly to in FIG. 12, envisages, for example, a progressive addition lens for the right eye with a spherical diopter S of 2.00, a cylindrical diopter C of −1.00, a cylindrical axis Ax of 180, an addition Add of 2.50, a progressive zone length of 14 mm, and a pupillary distance PD=32+32 mm.

In the contour line images of the illustrated example, a frame image 50 corresponding to the frame of a spectacle frame is reflected in each of the partial visual field areas. In the second embodiment, for example, by removing the pixel components constituting the simulation images obtained by performing the image processing on the original image, it is possible to create images obtained by overlaying the frame image 50 on the contour line images. The display-output content of such images enables the prospective spectacle lens wearer P1 who is looking at them to easily and accurately ascertain the distribution of the clearness index of the spectacle lens with respect to the position of the frame of the spectacle frame.

Figure 14:
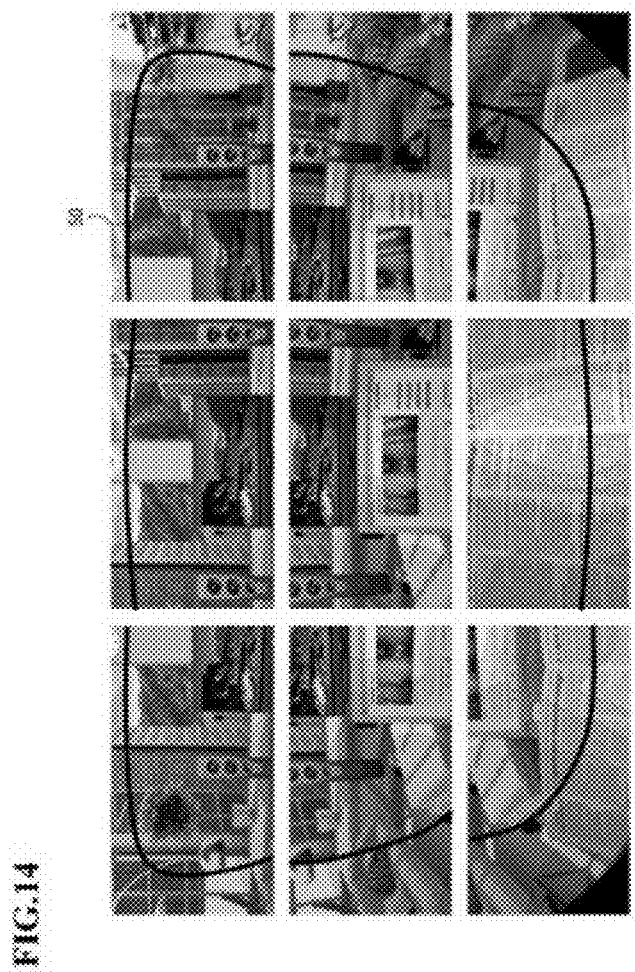
FIG. 14 is an explanatory diagram of images handled in simulation processing in the second embodiment of the present invention and illustrating a specific example in which a frame image is overlaid on simulation images separately for partial visual field areas superimposed with contour line images of a clearness index.

FIG. 14 is an explanatory diagram illustrating a specific example of a simulation image in each partial visual field area, on which contour line images are superimposed.

The images of the illustrated example are the simulation images of FIG. 12 with the contour line images of FIG. 13 superimposed thereon, and with the frame image 50 corresponding to the frame of a spectacle frame overlaid thereon. In the images of the illustrated example, the brightness of the images is adjusted according to the value of the clearness index. In the display screen unit 22 of the HMD 2, the simulation images with the contour line images superimposed thereon and the frame image 50 overlaid thereon, are selectively display-output in each partial visual field area.

The display-output content enable the prospective spectacle lens wearer P1 who is looking at them to easily and accurately ascertain the lens visual performance of the spectacle lens in a state in which the spectacle frame is being worn, and also to easily and accurately ascertain the distribution of the clearness index of the spectacle lens with respect to the position of the frame of the spectacle frame.

Advantageous Effects of Present Embodiment

The second embodiment obtains the following advantageous effects in addition to the advantageous effects obtained by the first embodiment as described above.

In the second embodiment, the image generation unit 35 of the server device 3 performs overlay processing of overlaying the frame image 50 of a spectacle frame on the simulation image, and simulation images on which the frame image 50 is overlaid, are displayed by the display screen unit 22 of the HMD 2. Thus the prospective spectacle lens wearer P1 is able to ascertain the lens visual performance of the spectacle lens while a state in which the spectacle frame is being worn is reproduced, obtaining a more appropriate simulated experience of a lens wearing state compared to cases in which the frame image 50 is not overlaid, and this is extremely highly convenient, and extremely beneficial in particular in cases in which simulation images are selectively displayed in each small visual field (partial visual field area). This is because there is a high probability that the frame portion of a spectacle frame is in the field of view for the partial visual field areas positioned at the perimeter edge side of the full visual field area, and, even in cases in which a simulation image is being displayed in such partial visual field areas, such a state is appropriately reproduced by overlaying the frame image 50 on the simulation image, and a virtual experience of a lens wearing state can be optimized.

C. Modified Examples

Although explanation has been given above of the first embodiment and the second embodiment of the present invention, the content disclosed above is merely exemplary embodiments of the present invention. Namely, the technical scope of the present invention is not limited by the exemplary embodiments described above.

For example, explanation has been given in each of the embodiments of examples of cases in which the display device that displays the simulation image is the HMD 2, however, as long as simulation images can be shown to the prospective spectacle lens wearer P1, the simulation images may be displayed using a display device other than the HMD 2 (for example, by using a stationary display device).

Moreover, although explanation has been given in each of the embodiments of examples of cases in which the terminal device that performs output of the explanatory information 36a etc. is the tablet terminal 1, as long as it is a terminal device capable of information input and output from and to the member of staff P2, output of the explanatory information 36a etc. may be performed using a terminal device other than the tablet terminal 1 (for example, a notebook or desktop type of personal computer).

Moreover, although explanation has been given in each of the embodiments of examples of cases in which notification is performed to the prospective spectacle lens wearer P1 by the explanatory information 36a, which is character information on the tablet terminal 1, being display-output to the member of staff P2, and the member of staff P2 reading out the display-output results of the explanatory information 36a, output of the explanatory information 36a may be performed in another manner, as long as it is ascertainable by the member of staff P2 or the prospective spectacle lens wearer P1. For example, in a case in which the terminal device that outputs the explanatory information 36a includes audio-output functionality, the member of staff P2 or the prospective spectacle lens wearer P1 may made to ascertain the explanatory information 36a through audio-output of the explanatory information 36a.

Moreover, although explanation has been given in each of the embodiments of examples of cases in which the member of staff P2 performs, on the tablet terminal 1, a selection operation for the small visual field worth (partial visual field area) to be displayed on the HMD 2, selection switching of the display content on the HMD 2 does not necessarily need to be by operation on the tablet terminal 1. Namely, for example, even without needing operation on the tablet terminal 1, automatic switching of display for each of the partial visual field areas every specific interval of time according to a predetermined sequence may be considered.

Moreover, although explanation has been given in each of the embodiments of examples of cases in which image data for the simulation images is received from the server device 3 by the tablet terminal 1, and, by transmitting to the HMD 2, display-output on the HMD 2, a configuration in which the HMD 2 and the server device 3 directly exchange image data may be considered. Namely, configuration may be made such that at least one out of the tablet terminal 1 or the HMD 2 constituting the simulation device 5 performs communication with the server device 3 over the communication network 4.

Moreover, although explanation has been given in each of the embodiments of examples of cases in which the server device 3 present on the communication network 4 is provided with the image generation unit 35 that generates the simulation images, and the explanatory information storage unit 36 that stores and retains the explanatory information 36a, and the simulation images and the explanatory information 36a arrive at the spectacle shop S side over the communication network 4 from the server device 3, the simulation images and the explanatory information 36a may be pre-held on the simulation device 5 employed on the spectacle shop S side. Namely, configuration may be considered which at least one out of the tablet terminal 1 or the HMD 2 constituting the simulation device 5 is equipped with an information storage unit for storing the simulation images and the explanatory information 36a separately for each of the partial visual field areas, and the simulation images and the explanatory information 36a are retrieved and output from the information storage unit as required.

Moreover, although explanation has been given in each of the embodiments of examples of cases in which the server device 3 is equipped with the lens design data generation unit 33, and processing from generation of the lens design data to generation of the simulation images is performed as one processing sequence, it is possible to perform the generation of lens design data and the generation of simulation images on completely different devices.

Moreover, although explanation has been given in each of the embodiments of examples of cases in which, on generation of and display-output of the simulation images, the full visual field area of the spectacle lens is segmented into nine partial visual field areas (small visual fields), there is no particular limitation to the number, manner, etc. of segmentation into small visual fields, and they may be any predetermined number, manner, etc.

Furthermore, although explanation has been given in each of the embodiments of examples of cases in which the original image storage unit 34 is segmented into the partial visual field areas (small visual fields) at the stage when the original image data 34a is stored and retained in the original image storage unit 34, segmentation into the partial visual field areas (small visual fields) may be performed at the latest before the stage of simulation image generation by the image processing unit 35a. Thus, for example, in cases in which the original image of the full visual field area is stored and retained as original image data 34a on the original image storage unit 34, a configuration may be considered in which simulation images are generated for partial visual field areas as the original images of the partial visual field areas are being extracted from the full visual field area.

Moreover, although explanation has been given in each of the embodiments of examples of cases in which, in the tablet terminal 1, the full visual field area worth of the original image 13a, the enlarged small visual field worth of the simulation image 13b, and the text image 13c for the explanatory information are display-output in next to each other on the display screen of the touch panel 12, there is no particular limitation to the output layout on the display screen, and configuration may be considered in which the individual display content is modified as required. For example, although explanation has been given in each of the embodiments of examples of cases in which display-output for the small visual field worth of the simulation image 13b has the contour lines of the clearness index of the spectacle lens superimposed thereon, superimposition of the contour line images is not necessary, and the simulation images may be display-output in a state in which the contour line images are not superimposed. Similar applies to the display-output content of the display screen unit 22 of the HMD 2. Namely, in the display screen unit 22 of the HMD 2, a simulated experience a lens wearing state may be given to the prospective spectacle lens wearer P1 by displaying the simulation images as output in a state in which the contour line images are not superimposed.

Moreover, although explanation has been given in each of the embodiments of examples of cases in which the image processing unit 35a generates simulation images by performing image processing to reflect the lens visual performance (blur, distortion, etc.) on the original image data 34a, other image processing may also be performed at simulation image generation. An example of the other image processing is image processing to render effects of polarization, photochromatic, etc. Performing such incidental image processing enables generation of simulation images close to natural images even if the original image data 34a is the data regarding a CG image.

EXPLANATION OF THE REFERENCE NUMERALS

1 . . . tablet terminal (terminal device), 2 . . . HMD (display device), 11 . . . communication I/F unit, 12 . . . touch panel, 12a . . . information output unit, 12b . . . operation unit, 12c . . . information input unit, 13a . . . full visual field area of original image, 13b . . . small visual field worth of simulation image, 13c . . . explanatory information image, 21 . . . communication I/F unit, 22 . . . display screen unit, 3 . . . server device, 4 . . . communication network, 5 . . . simulation device, 31 . . . communication I/F unit, 32 . . . acquired information recognition unit, 33 . . . lens design data generation unit, 34 . . . original image storage unit, 34a . . . original image data, 35 . . . image generation unit, 35a . . . image processing unit, 35b . . . image superimposition unit, 36 . . . explanatory information storage unit, 36a . . . explanatory information, 37 . . . control unit, P1 . . . prospective spectacle lens wearer, P2 . . . member of staff, S . . . spectacle shop.

The invention claimed is:

1. A simulation system, comprising:
a server device including functionality of a computer, the server device including:
an image generation unit that, based on lens design data of a spectacle lens a prospective spectacle lens wearer visiting a spectacle shop is scheduled to wear, divides a full visual field area of the spectacle lens into a plurality of partial visual field areas, performs image processing on an original image for each of the plurality of partial visual field areas to reflect lens visual performance of the spectacle lens, and generates a simulation image separately for each of the plurality of partial visual field areas; and
an information storage unit that stores explanatory information regarding characteristics of the lens visual performance for each of the plurality of partial visual field areas, classified by sort of lens design standard applied to the lens design data;
a display device connected to the server device, the display device including a display screen unit that selectively displays each simulation image separately for each of the plurality of partial visual field areas so that the prospective spectacle lens wearer can check them by sight; and
a terminal device provided in the spectacle shop and connected to the server device and the display device, the terminal device including an information output unit that outputs the explanatory information acquired from the information storage unit corresponding to the simulation image being displayed on the display screen unit of the display device.

2. The simulation system of claim 1, wherein:
the image generation unit of the server device performs superimposition processing of contour lines of a clearness index of the spectacle lens onto the simulation image; and
the display screen unit of the display device displays the simulation image with the contour lines superimposed.

3. The simulation system of claim 1, wherein
the image generation unit of the server device performs overlay processing of overlaying a frame image of a spectacle frame on the simulation image for holding the spectacle lens; and
the display screen unit of the display device displays the simulation image on which the frame image is overlaid.

4. The simulation system of claim 1, wherein:
the display device is a head mounted display device worn on the head of the prospective spectacle lens wearer; and
the display screen unit performs image display individually for a left eye and a right eye of the prospective spectacle lens wearer.

5. The simulation system of claim 1, wherein:
the terminal device is a portable information terminal used by a member of staff of the spectacle shop; and
the information output unit displays output of the explanatory information to the member of staff.

6. The simulation system of claim 1, wherein:
the information output unit audio-outputs the explanatory information.

7. The simulation system of claim 1, wherein an operation unit for performing a selection operation of a simulation image to display on the display device is provided to at least one of the display device and the terminal device.

8. The simulation system of claim 1, wherein:
the terminal device includes an information input unit for inputting parameter information for the spectacle lens scheduled to be worn by the prospective spectacle lens wearer; and
the server device includes a data generation unit that, based on the parameter information that has been input by the information input unit, identifies a sort of lens design standard that should be applied to the spectacle lens scheduled to be worn by the prospective spectacle lens wearer, and that generates lens design data of the spectacle lens while applying a lens design standard of the identified sort.

9. A simulation device, comprising:
a display device enabling visual recognition of a simulation image by a prospective spectacle lens wearer visiting a spectacle shop, the display device including a display screen unit that selectively displays the simulation image, obtained by dividing a full visual field area of a spectacle lens into a plurality of partial visual field areas and performing image processing to reflect lens visual performance of the spectacle lens on an original image for each of the plurality of partial visual field areas, separately for each of the partial visual field areas, to enable the prospective spectacle lens wearer to check it by sight; and
a terminal device provided in a spectacle shop and connected to the display device, the terminal device including an information output unit that outputs explanatory information regarding characteristics of the lens visual performance reflected in the simulation image being displayed on the display screen unit of the display device.

10. The simulation device of claim 9, wherein:
at least one of the terminal device and the display device is connected to a communication network and includes a communication interface that performs communication with a server device over the communication network; and
configuration is made such that at least the simulation image and the explanatory information is acquired from the server device through the communication interface separately for each of the partial visual field areas.

11. The simulation device of claim 9, wherein at least one out of the terminal device or the display device includes an information storage unit that stores the simulation image and the explanatory information separately for each of the partial visual field areas.

12. A product explanation assistance method for assisting a product explanation during a product explanation performed at a spectacle shop, by using a terminal device employed in the spectacle shop, and a display device for visually recognizing a simulation image by a prospective spectacle lens wearer visiting the spectacle shop, the product explanation assistance method comprising:

displaying on a display device a simulation image, obtained by dividing a full visual field area of a spectacle lens into a plurality of partial visual field areas and performing image processing to reflect lens visual performance of the spectacle lens on an original image for each of the plurality of partial visual field areas, selectively and separately for each of the plural partial visual field areas, to enable the prospective spectacle lens wearer to check it by sight;

an information output step of acquiring from an information storage unit, and outputting to the terminal device, explanatory information regarding characteristics of the lens visual performance reflected in the simulation image displayed on the display device that has been stored in advance in association with the partial visual field areas; and a selection switching step of switching selection of simulation images for display on the display device and correspondingly switching explanatory information output by the terminal device.

* * * * *